US008278283B2

(12) United States Patent
Seth et al.

(10) Patent No.: US 8,278,283 B2
(45) Date of Patent: Oct. 2, 2012

(54) 6-DISUBSTITUTED OR UNSATURATED BICYCLIC NUCLEIC ACID ANALOGS

(75) Inventors: Punit P. Seth, Carlsbad, CA (US); Eric E. Swayze, Encinitas, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 174 days.

(21) Appl. No.: 12/667,684

(22) PCT Filed: Jul. 1, 2008

(86) PCT No.: PCT/US2008/068922
§ 371 (c)(1),
(2), (4) Date: Nov. 10, 2010

(87) PCT Pub. No.: WO2009/006478
PCT Pub. Date: Jan. 8, 2009

(65) Prior Publication Data
US 2011/0053881 A1    Mar. 3, 2011

Related U.S. Application Data

(60) Provisional application No. 60/948,134, filed on Jul. 5, 2007.

(51) Int. Cl.
A01N 43/04      (2006.01)
A61K 31/70      (2006.01)
C12N 15/11      (2006.01)
C07H 19/00      (2006.01)
C07H 21/02      (2006.01)

(52) U.S. Cl. .......... 514/42; 514/43; 514/44 A; 536/22.1; 536/23.1; 536/24.5; 536/26.1; 536/27.1

(58) Field of Classification Search .................. None
See application file for complete search history.

(56) References Cited

U.S. PATENT DOCUMENTS

| | | |
|---|---|---|
| 3,687,808 A | 8/1972 | Merigan et al. |
| 4,415,732 A | 11/1983 | Caruthers et al. |
| 4,458,066 A | 7/1984 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,668,777 A | 5/1987 | Caruthers et al. |
| 4,725,677 A | 2/1988 | Koster et al. |
| 4,845,205 A | 7/1989 | Huynh Dinh et al. |
| 4,973,679 A | 11/1990 | Caruthers et al. |
| 4,981,957 A | 1/1991 | Lebleu et al. |
| 5,013,830 A | 5/1991 | Ohtsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,069 E | 9/1992 | Koster et al. |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,185,444 A | 2/1993 | Summerton et al. |
| 5,188,897 A | 2/1993 | Suhadolnik et al. |
| 5,194,599 A | 3/1993 | Froehler et al. |
| 5,214,134 A | 5/1993 | Weis et al. |
| 5,216,141 A | 6/1993 | Benner |
| 5,220,007 A | 6/1993 | Pederson et al. |
| 5,235,033 A | 8/1993 | Summerton et al. |
| 5,256,775 A | 10/1993 | Froehler |
| 5,264,423 A | 11/1993 | Cohen et al. |
| 5,264,562 A | 11/1993 | Matteucci |
| 5,264,564 A | 11/1993 | Matteucci |
| 5,276,019 A | 1/1994 | Cohen et al. |
| 5,278,302 A | 1/1994 | Caruthers et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,378,825 A | 1/1995 | Cook et al. |
| 5,386,023 A | 1/1995 | Sanghvi et al. |
| 5,393,878 A | 2/1995 | Leumann |

(Continued)

FOREIGN PATENT DOCUMENTS

WO      WO 94/02499       2/1994

(Continued)

OTHER PUBLICATIONS

Bass et al., "Double-Stranded RNA as a Template for Gene Silencing" Cell (2000) 101:235-238.
Beaucage et al., "The Functionalization of Oligonucleotides Via Phosphoroamidite Derivatives" Tetrahedron (1993) 49(10):1925-1963.
Beaucage et al., "The Synthesis of Specific Ribonucleotides and Unrelated Phosphorylated Biomolecules by the Phosphoramidite Method" Tetrahedron (1993) 49(46):10441-10488.
Beaucage et al., "Advances in the Synthesis of Oligonucleotides by the Phosphoramidite Approach" Tetrahedron (1992) 48(12):2223-2311.

(Continued)

Primary Examiner — Traviss C McIntosh, III
(74) Attorney, Agent, or Firm — Isis Pharmaceuticals, Inc.

(57) ABSTRACT

The present disclosure describes 6-disubstituted bicyclic nucleosides, oligomeric compounds prepared therefrom and methods of using the oligomeric compounds. More particularly, the 6-disubstituted bicyclic nucleosides each comprise a 2'-O—C(Ri)(R2)-4' or 2'-O—C=(R3)(R.4)-4' bridge wherein each R is, independently a substituent group and Ri and R2 include H. The 6-disubstituted bicyclic nucleosides are useful for enhancing properties of oligomeric compounds including nuclease resistance. In certain embodiments, the oligomeric compounds provided herein hybridize to a portion of a target RNA resulting in loss of normal function of the target RNA.

44 Claims, No Drawings

U.S. PATENT DOCUMENTS

| | | | |
|---|---|---|---|
| 5,399,676 A | 3/1995 | Froehler | |
| 5,403,711 A | 4/1995 | Walder et al. | |
| 5,405,938 A | 4/1995 | Summerton et al. | |
| 5,405,939 A | 4/1995 | Suhadolnik et al. | |
| 5,432,272 A | 7/1995 | Benner | |
| 5,434,257 A | 7/1995 | Matteucci et al. | |
| 5,446,137 A | 8/1995 | Maag et al. | |
| 5,453,496 A | 9/1995 | Caruthers et al. | |
| 5,455,233 A | 10/1995 | Spielvogel et al. | |
| 5,457,187 A | 10/1995 | Gmeiner et al. | |
| 5,459,255 A | 10/1995 | Cook et al. | |
| 5,466,677 A | 11/1995 | Baxter et al. | |
| 5,466,786 A | 11/1995 | Buhr et al. | |
| 5,470,967 A | 11/1995 | Huie et al. | |
| 5,476,925 A | 12/1995 | Letsinger et al. | |
| 5,484,908 A | 1/1996 | Froehler et al. | |
| 5,489,677 A | 2/1996 | Sanghvi et al. | |
| 5,491,133 A | 2/1996 | Walder et al. | |
| 5,502,177 A | 3/1996 | Matteucci et al. | |
| 5,508,270 A | 4/1996 | Baxter et al. | |
| 5,514,785 A | 5/1996 | Van Ness et al. | |
| 5,519,126 A | 5/1996 | Hecht | |
| 5,519,134 A | 5/1996 | Acevedo et al. | |
| 5,525,711 A | 6/1996 | Hawkins et al. | |
| 5,527,899 A | 6/1996 | Froehler | |
| 5,536,821 A | 7/1996 | Agrawal et al. | |
| 5,541,306 A | 7/1996 | Agrawal et al. | |
| 5,541,307 A | 7/1996 | Cook et al. | |
| 5,550,111 A | 8/1996 | Suhadolnik et al. | |
| 5,552,540 A | 9/1996 | Haralambidis | |
| 5,561,225 A | 10/1996 | Maddry et al. | |
| 5,563,253 A | 10/1996 | Agrawal et al. | |
| 5,565,350 A | 10/1996 | Kmiec | |
| 5,565,555 A | 10/1996 | Froehler et al. | |
| 5,567,811 A | 10/1996 | Misiura et al. | |
| 5,571,799 A | 11/1996 | Tkachuk et al. | |
| 5,576,427 A | 11/1996 | Cook et al. | |
| 5,587,361 A | 12/1996 | Cook et al. | |
| 5,587,469 A | 12/1996 | Cook et al. | |
| 5,591,722 A | 1/1997 | Montgomery et al. | |
| 5,594,121 A | 1/1997 | Froehler et al. | |
| 5,596,086 A | 1/1997 | Matteucci et al. | |
| 5,596,091 A | 1/1997 | Switzer | |
| 5,597,909 A | 1/1997 | Urdea et al. | |
| 5,602,240 A | 2/1997 | De Mesmaker et al. | |
| 5,608,046 A | 3/1997 | Cook et al. | |
| 5,610,289 A | 3/1997 | Cook et al. | |
| 5,610,300 A | 3/1997 | Altmann et al. | |
| 5,614,617 A | 3/1997 | Cook et al. | |
| 5,618,704 A | 4/1997 | Sanghvi et al. | |
| 5,623,065 A | 4/1997 | Cook et al. | |
| 5,623,070 A | 4/1997 | Cook et al. | |
| 5,625,050 A | 4/1997 | Beaton et al. | |
| 5,627,053 A | 5/1997 | Usman et al. | |
| 5,633,360 A | 5/1997 | Bischofberger et al. | |
| 5,639,873 A | 6/1997 | Barascut et al. | |
| 5,645,985 A | 7/1997 | Froehler et al. | |
| 5,646,265 A | 7/1997 | McGee | |
| 5,646,269 A | 7/1997 | Matteucci et al. | |
| 5,652,355 A | 7/1997 | Metelev et al. | |
| 5,652,356 A | 7/1997 | Agrawal | |
| 5,658,873 A | 8/1997 | Bertsch-Frank et al. | |
| 5,663,312 A | 9/1997 | Chaturvedula | |
| 5,670,633 A | 9/1997 | Cook et al. | |
| 5,672,697 A | 9/1997 | Buhr et al. | |
| 5,677,437 A | 10/1997 | Teng et al. | |
| 5,677,439 A | 10/1997 | Weis et al. | |
| 5,681,941 A | 10/1997 | Cook et al. | |
| 5,700,920 A | 12/1997 | Altmann et al. | |
| 5,700,922 A | 12/1997 | Cook | |
| 5,721,218 A | 2/1998 | Froehler | |
| 5,750,692 A | 5/1998 | Cook et al. | |
| 5,763,588 A | 6/1998 | Matteucci et al. | |
| 5,792,608 A | 8/1998 | Swaminathan et al. | |
| 5,792,747 A | 8/1998 | Schally et al. | |
| 5,830,653 A | 11/1998 | Froehler et al. | |
| 6,005,096 A | 12/1999 | Matteucci et al. | |
| 6,268,490 B1 | 7/2001 | Imanishi et al. | |
| 6,426,220 B1 | 7/2002 | Bennett et al. | |
| 6,600,032 B1 | 7/2003 | Manoharan et al. | |
| 6,770,748 B2 | 8/2004 | Imanishi et al. | |
| 6,794,499 B2 | 9/2004 | Wengel et al. | |
| 7,053,207 B2 | 5/2006 | Wengel | |
| 7,399,845 B2 * | 7/2008 | Seth et al. | 536/22.1 |
| 2003/0082807 A1 | 5/2003 | Wengel | |
| 2003/0105309 A1 | 6/2003 | Imanishi et al. | |
| 2003/0207841 A1 | 11/2003 | Kaneko et al. | |
| 2003/0224377 A1 | 12/2003 | Wengel et al. | |
| 2004/0014959 A1 | 1/2004 | Sorensen et al. | |
| 2004/0143114 A1 | 7/2004 | Imanishi et al. | |
| 2004/0192918 A1 | 9/2004 | Imanishi et al. | |
| 2004/0219565 A1 | 11/2004 | Kauppinen et al. | |

FOREIGN PATENT DOCUMENTS

| | | |
|---|---|---|
| WO | WO 94/17093 | 8/1994 |
| WO | WO 2005121372 | 11/2005 |
| WO | WO 2005121371 | 12/2005 |
| WO | WO 2007134181 | 11/2007 |

OTHER PUBLICATIONS

Chiang et al., "Antisense Oligonucleotides Inhibit Intercellular Adhesion Molecule 1 Expression by Two Distinct Mechanisms" J. Biol. Chem. (1991) 266(27):18162-18171.

Elbashir et al., "Duplexes of 21-nucleotide RNAs mediate RNA interference in cultured mammalian cells" Nature (2001) 411:494-498.

Elbashir et al., "RNA interference is mediated by 21- and 22-nucleotide RNAs" Genes Dev. (2001) 15:188-200.

Englisch et al., "Chemically Modified Oligonucleotides as Probes and Inhibitors" Angewandte Chemie, International Edition (1991) 30:613.

Fire et al., "Potent and specific genetic interference by double-stranded RNA in *Caenorhabditis elegans*" Nature (1998) 391:806-811.

Gait et al., "Applications of Chemically Synthesized RNA" in RNA: Protein Interactions, Ed. Smith (1998) 1-36.

Gallo et al., "2'-C-Methyluridine phosphoramidite: a new building block for the preparation of RNA analogues carrying the 2'-hydroxyl group" Tetrahedron (2001) 57:5707-5713.

Koshkin et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition" Tetrahedron (1998) 54:3607-3630.

Kroschwitz, The Concise Encyclopedia of Polymer Science and Engineering, John Wiley & Sons, 1990, pp. 858-859.

Kumar et al., "The First Analogues of LNA (Locked Nucleic Acids): Phosphorothioate-LNA and 2'-Thio-LNA" Bioorg. Med. Chem. Lett. (1998) 8:2219-2222.

Montgomery et al., "RNA as a target of double-stranded RNA-mediated genetic interference in *Caenorhabditis elegans*" PNAS (1998) 95:15502-15507.

Nishikura et al., "A Short Primer on RNAi: RNA-Directed RNA Polymerase Acts as a Key Catalyst" Cell (2001) 107:415-416.

Sanghvi etal., Antisense Research and Applications, Crooke & Lebleu ed., CRC Press, 1993, Chapter 15.

Scaringe, "RNA Oligonucleotide Synthesis via 5'-Silyl-2'-Orthoester Chemistry" Methods (2001) 23:206-217.

Singh et al., "LNA (locked nucleic acids): synthesis and high-affinity nucleic acid recognition" Chem. Commun. (1998) 4:455-456.

Singh et al., "Synthesis of 2'-Amino-LNA: A Novel Conformationally Restricted High-Affinity Oligonucleotide Analogue with a Handle" J. Org. Chem. (1998) 63(26):10035-10039.

Tabara et al., "RNAi in *C. elegans*: Soaking in the Genome Sequence" Science (1998) 282:430-431.

Tijsterman et al., "RNA Helicase MUT-14-Dependent Gene Silencing Triggered in *C. elegans* by Short Antisense RNAs" Science (2002) 295:694-697.

Timmons et al., "Specific interference by ingested dsRNA" Nature (1998) 395:854.

Timmons et al., "Ingestion of bacterially expressed dsRNAs can produce specific and potent genetic interference in *Caenorhabditis elegans*" Gene (2001) 263:103-112.

Tuschl et al., "Targeted mRNA degradation by double-stranded RNA in vitro" Genes Dev. (1999) 13:3191-3197.

Wahlestedt et al., "Potent and nontoxic antisense oligonucleotides containing locked nucleic acids" PNAS (2000) 97(10):5633-5638.

Wengel et al., "Chemistry of locked nucleic acids (LNA): Design, synthesis, and bio-physical properties" International Journal of Peptide Research and Therapeutics (2003) 10(3-4):237-253.

International Search Report for application PCT/US2008/068922 dated Dec. 29, 2008.

* cited by examiner

6-DISUBSTITUTED OR UNSATURATED BICYCLIC NUCLEIC ACID ANALOGS

CROSS-REFERENCE TO RELATED APPLICATIONS

This application is the national phase entry pursuant to 35 U.S.C. §371 of International Application No. PCT/US2008/068922, filed Jul. 1, 2008, which claims the benefit of U.S. Provisional Application No. 60/948,134, filed Jul. 5, 2007, entitled "6-Disubstituted or Unsaturated Bicyclic Nucleic Acid Analogs", all of which are incorporated herein by reference.

SEQUENCE LISTING

The present application is being filed along with a Sequence Listing in electronic format. The Sequence Listing is provided as a file entitled CHEM0039WOSEQ.txt, created on Jul. 1, 2008 which is 6 Kb in size. The information in the electronic format of the sequence listing is incorporated herein by reference in its entirety.

FIELD OF THE INVENTION

Provided herein are 6-disubstituted bicyclic nucleosides, oligomeric compounds prepared therefrom and methods of using the oligomeric compounds. More particularly, the 6-disubstituted bicyclic nucleosides each comprise a 2'-O—C($R_1$)($R_2$)-4' or 2'-O—C=($R_3$)($R_4$)-4' bridge wherein each R is, independently a substituent group and $R_1$ and $R_2$ include H. In certain embodiments, the oligomeric compounds hybridize to a portion of a target RNA resulting in loss of normal function of the target RNA.

BACKGROUND OF THE INVENTION

Antisense technology is an effective means for reducing the expression of one or more specific gene products and can therefore prove to be uniquely useful in a number of therapeutic, diagnostic, and research applications. Chemically modified nucleosides are routinely used for incorporation into antisense sequences to enhance one or more properties such as for example nuclease resistance, binding affinity or reduced toxicity profile. One such group of chemical modifications includes bicyclic nucleosides wherein the furanose portion of the nucleoside includes a bridge connecting two atoms on the furanose ring thereby forming a bicyclic ring system. Such bicyclic nucleosides have various names including BNA's and LNA's for bicyclic nucleic acids or locked nucleic acids respectively.

Various BNA's have been prepared and reported in the patent and scientific literature, see for example: Singh et al., Chem. Commun., 1998, 4, 455-456; Koshkin et al., Tetrahedron, 1998, 54, 3607-3630; Wahlestedt et al., Proc. Natl. Acad. Sci. U.S.A., 2000, 97, 5633-5638; Kumar et al., Bioorg. Med. Chem. Lett., 1998, 8, 2219-2222; Wengel et al., PCT International Application WO 98-DK393 19980914; Singh et al., J. Org. Chem., 1998, 63, 10035-10039, the text of each is incorporated by reference herein, in their entirety. Examples of issued US patents and published applications include for example: U.S. Pat. Nos. 7,053,207, 6,770,748, 6,268,490 and 6,794,499 and published U.S. applications 20040219565, 20040014959, 20030207841, 20040192918, 20030224377, 20040143114 and 20030082807; the text of each is incorporated by reference herein, in their entirety.

Many LNA's are toxic. See, e.g., Swayze, E. E.; Siwkowski, A. M.; Wancewicz, E. V.; Migawa, M. T.; Wyrzykiewicz, T. K.; Hung, G.; Monia, B. P.; Bennett, C. F., Antisense oligonucleotides containing locked nucleic acid improve potency but cause significant hepatotoxicity in animals. Nucl. Acids Res., doi: 10.1093/nar/gkl1071 (December 2006, advanced online publication).

Consequently, there remains a long-felt need for agents that specifically regulate gene expression via antisense mechanisms. Disclosed herein are 6-disubstituted or unsaturated BNA's and antisense compounds prepared therefrom useful for modulating gene expression pathways, including those relying on mechanisms of action such as RNaseH, RNAi and dsRNA enzymes, as well as other antisense mechanisms based on target degradation or target occupancy. One having skill in the art, once armed with this disclosure will be able, without undue experimentation, to identify, prepare and exploit antisense compounds for these uses.

BRIEF SUMMARY OF THE INVENTION

Provided herein are 6-disubstituted bicyclic nucleosides, oligomeric compounds comprising these bicyclic nucleosides and methods of using the oligomeric compounds. In certain embodiments, the bicyclic nucleosides impart enhanced properties to oligomeric compounds they are incorporated into.

The variables are defined individually in further detail herein. It is to be understood that the bicyclic nucleosides, oligomer compounds, and methods of use thereof provided herein include all combinations of the embodiments disclosed and variables defined herein.

In certain embodiments, bicyclic nucleosides are provided having Formula I:

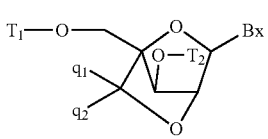

wherein:
Bx is a heterocyclic base moiety;
one of $T_1$ and $T_2$ is H or a hydroxyl protecting group and the other of $T_1$ and $T_2$ is H, a hydroxyl protecting group or a reactive phosphorus group;
$q_1$ and $q_2$ are each, independently, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_1$, $SJ_1$, $SOJ_1$, $SO_2J_1$, $NJ_1J_2$, $N_3$, CN, C(=O)$OJ_1$, C(=O)$NJ_1J_2$, C(=O)$J_1$, N(H)C(=NH)$NJ_1J_2$, N(H)C(=O)$NJ_1J_2$ or N(H)C(=S)$NJ_1J_2$;
or $q_1$ and $q_2$ together are =C($q_3$)($q_4$);
$q_3$ and $q_4$ are each, independently, H, halogen, $C_1$-$C_{12}$ alkyl or substituted $C_1$-$C_{12}$ alkyl;
each substituted group is, independently, mono or poly substituted with substituent groups independently selected from halogen, $C_1$-$C_6$ alkyl, $C_2$-$C_6$ alkenyl, $C_2$-$C_6$ alkynyl, $SJ_1$, $NJ_1J_2$, $N_3$, CN, C(=O)$OJ_1$, C(=O)$NJ_1J_2$, C(=O)$J_1$, O—C(=O)$NJ_1J_2$, N(H)C(=O)$NJ_1J_2$ or N(H)C(=S)$NJ_1J_2$; and
each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group.

In certain embodiments, at least one of $q_1$ and $q_2$ is $C_1$-$C_6$ alkyl or substituted $C_1$-$C_6$ alkyl. In certain embodiments, $q_1$ and $q_2$ are each, independently, $C_1$-$C_6$ alkyl or substituted $C_1$-$C_6$ alkyl. In certain embodiments, on and $q_2$ are each, independently, methyl, ethyl or propyl. In certain embodiments, $q_1$ and $q_2$ are each methyl. In certain embodiments, at least one of $q_1$ and $q_2$ is substituted $C_1$-$C_6$ alkyl.

In certain embodiments, at least one of $q_1$ and $q_2$ is substituted $C_1$-$C_6$ alkyl. In certain embodiments, at least one of $q_1$ and $q_2$ is substituted $C_1$-$C_6$ alkyl wherein the substituent group is selected from $OJ_1$, $SJ_1$, $NJ_1J_2$, $N_3$, CN, $C(=O)OJ_1$, $C(=O)NJ_1J_2$, $C(=O)J_1$ or $O—C(=O)NJ_1J_2$ wherein each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group. In certain embodiments, at least one of $q_1$ and $q_2$ is substituted $C_1$-$C_6$ alkyl wherein the substituent group is selected from $OJ_1$, $NJ_1J_2$ or CN wherein each $J_1$ and $J_2$ is, independently, H, $C_1$-$C_6$ alkyl or a protecting group.

In certain embodiments, $q_1$ and $q_2$ together, are $=C(q_3)(q_4)$. In certain embodiments, $q_3$ and $q_4$ are each H. In certain embodiments, at least one of $q_3$ and $q_4$ is halogen, $C_1$-$C_6$ alkyl or substituted $C_1$-$C_6$ alkyl. In certain embodiments, at least one of $q_3$ and $q_4$ is methyl. In certain embodiments, $q_3$ and $q_4$ are each methyl.

In certain embodiments, each of $T_1$ and $T_2$ is a hydroxyl protecting group. In certain embodiments, each of said hydroxyl protecting groups is, independently, selected from acetyl, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, benzoyl, p-phenylbenzoyl, 2,6-dichlorobenzyl, diphenylmethyl, p-nitrobenzyl, trimethylsilyl, triethylsilyl, t-butyldimethylsilyl, t-butyldiphenylsilyl, triphenylsilyl, triisopropylsilyl, benzoylformate, chloroacetyl, trichloroacetyl, trifluoroacetyl, pivaloyl, 9-fluorenylmethyl carbonate, mesylate, tosylate, triflate, trityl, monomethoxytrityl, dimethoxytrityl, trimethoxytrityl or substituted pixyl. In certain embodiments, $T_1$ is acetyl, benzyl, t-butyldimethylsilyl, t-butyldiphenylsilyl or 4,4'-dimethoxytrityl. In certain embodiments, $T_1$ is 4,4'-dimethoxytrityl.

In certain embodiments, $T_2$ is a reactive phosphorus group. In certain embodiments, $T_2$ is a reactive phosphorus group selected from is diisopropylcyanoethoxy phosphoramidite or H-phosphonate. In certain embodiments, $T_2$ is diisopropylcyanoethoxy phosphoramidite. In certain embodiments, $T_2$ is diisopropylcyanoethoxy phosphoramidite and $q_1$ and $q_2$ are each methyl. In certain embodiments, $T_2$ is diisopropylcyanoethoxy phosphoramidite and $q_1$ and $q_2$ together, are $=C(q_3)(q_4)$ and $q_3$ and $q_4$ are each H.

In certain embodiments, Bx is a pyrimidine, substituted pyrimidine, purine or substituted purine. In certain embodiments, Bx is uracil, 5-methyluracil, 5-propynyl-uracil, 5-thiazolo-uracil, thymine, cytosine, 5-methylcytosine, 5-propynyl-cytosine, 5-thiazolo-cytosine, adenine, guanine or 2,6-diaminopurine.

In certain embodiments, each $J_1$ and $J_2$ is, independently, H or $C_1$-$C_3$ alkyl.

In certain embodiments, bicyclic nucleosides are provided having Formula II:

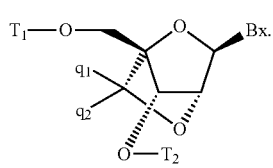

II

In certain embodiments, oligomeric compound are provided comprising at least one bicyclic nucleoside having Formula III:

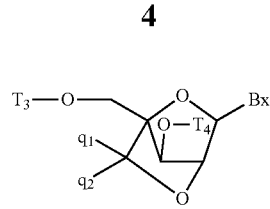

III wherein independently for each of said at least one bicyclic nucleoside having Formula III:

Bx is a heterocyclic base moiety;

$T_3$ and $T_4$ are each, independently, an internucleoside linking group linking the bicyclic nucleoside having Formula III to the oligomeric compound or one of $T_3$ and $T_4$ is an internucleoside linking group linking the bicyclic nucleoside having Formula III to the oligomeric compound and the other of $T_3$ and $T_4$ is H, a hydroxyl protecting group, a linked conjugate group or a 5' or 3'-terminal group;

$q_1$ and $q_2$ are each, independently, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_1$, $SJ_1$, $SOJ_1$, $SO_2J_1$, $NJ_1J_2$, $N_3$, CN, $C(=O)OJ_1$, $C(=O)NJ_1J_2$, $C(=O)J_1$, $O—C(=O)NJ_1J_2$, $N(H)C(=NH)NJ_1J_2$, $N(H)C(=O)NJ_1J_2$ or $N(H)C(=S)NJ_1J_2$;

or $q_1$ and $q_2$ together are $=C(q_3)(q_4)$;

$q_3$ and $q_4$ are each, independently, H, halogen, $C_1$-$C_{12}$ alkyl or substituted $C_1$-$C_{12}$ alkyl;

each substituted group is, independently, mono or poly substituted with substituent groups independently selected from halogen, $C_1$-$C_6$ alkyl, $C_2$-$C_6$ alkenyl, $C_2$-$C_6$ alkynyl, $OJ_1$, $SJ_1$, $NJ_1J_2$, $N_3$, CN, $C(=O)J_1$, $C(=O)NJ_1J_2$, $C(=O)J_1$, $O—C(=O)NJ_1J_2$, $N(H)C(=O)NJ_1J_2$ or $N(H)C(=S)NJ_1J_2$; and each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group.

In certain embodiments, oligomeric compounds are provided each comprising at least one bicyclic nucleoside having Formula III wherein at least one of $q_1$ and $q_2$ is $C_1$-$C_6$ alkyl or substituted $C_1$-$C_6$ alkyl. In certain embodiments, each $q_1$ and $q_2$ is, independently, $C_1$-$C_6$ alkyl or substituted $C_1$-$C_6$ alkyl. In certain embodiments, each $q_1$ and $q_2$ is, independently, methyl, ethyl or propyl. In certain embodiments, each $q_1$ and $q_2$ is methyl.

In certain embodiments, oligomeric compounds are provided each comprising at least one bicyclic nucleoside having Formula III wherein at least each $q_1$ or each $q_2$ is substituted $C_1$-$C_6$ alkyl. In certain embodiments, at least each $q_1$ or each $q_2$ is substituted $C_1$-$C_6$ alkyl wherein the substituent group is selected from $OJ_1$, $SJ_1$, $NJ_1J_2$, $N_3$, CN, $C(=O)OJ_1$, $C(=O)NJ_1J_2$, $C(=O)J_1$ or $O—C(=O)NJ_1J_2$ wherein each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group. In certain embodiments, at least each $q_1$ or each $q_2$ is substituted $C_1$-$C_6$ alkyl wherein the substituent group is selected from $OJ_1$, $NJ_1J_2$ or CN wherein each $J_1$ and $J_2$ is, independently, H, $C_1$-$C_6$ alkyl or a protecting group.

In certain embodiments, oligomeric compounds are provided each comprising at least one bicyclic nucleoside having Formula III wherein for each bicyclic nucleoside $q_1$ and $q_2$ together are $=C(q_3)(q_4)$. In certain embodiments, each $q_3$ and each $q_4$ is H. In certain embodiments, at least each $q_3$ or each $q_4$ is halogen, $C_1$-$C_6$ alkyl or substituted $C_1$-$C_6$ alkyl. In certain embodiments, at least each $q_3$ or each $q_4$ is methyl. In certain embodiments, each $q_3$ and each $q_4$ is methyl.

In certain embodiments, oligomeric compounds are provided each comprising at least one bicyclic nucleoside having Formula III and further comprising at least one 3' or 5'-terminal group.

In certain embodiments, oligomeric compounds are provided each comprising at least one bicyclic nucleoside having Formula III and further comprising a continuous sequence of linked nucleosides wherein each internucleoside linking group is, independently, a phosphodiester or phosphorothioate. In certain embodiments, each internucleoside linking group is a phosphorothioate.

In certain embodiments, oligomeric compounds are provided each comprising at least one bicyclic nucleoside having Formula IV:

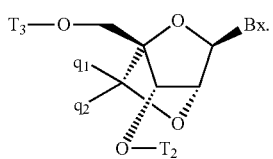

IV

In certain embodiments, oligomeric compounds are provided each comprising at least one region of at least two contiguous bicyclic nucleosides having Formula III. In certain embodiments, the at least one region of at least two contiguous bicyclic nucleosides having Formula III is located at the 3' or the 5'-end of the oligomeric compound. In certain embodiments, the at least one region of at least two contiguous bicyclic nucleosides having Formula III is located at the 3' or the 5'-end of the oligomeric compound and at least one bicyclic nucleoside having Formula III located at the other of the 3' or the 5'-end of the oligomeric compound.

In certain embodiments, gapped oligomeric compounds are provided each having an internal region of from about 6 to about 14 monomeric subunits separating two external regions independently comprising from 1 to about 5 contiguous bicyclic nucleosides having Formula III. In certain embodiments, essentially each monomeric subunit in the internal region is a β-D-2'-deoxyribonucleoside. In certain embodiments, the internal region comprises from about 8 to about 14 β-D-2'-deoxyribonucleosides. In certain embodiments, the internal region comprises from about 10 to about 14 β-D-2'-deoxyribonucleosides. In certain embodiments, the internal region comprises from about 10 to about 12 β-D-2'-deoxyribonucleosides. In certain embodiments, the internal region comprises from about 10 to about 12 β-D-2'-deoxyribonucleosides and each external region independently comprises from 2 to about 3 bicyclic nucleosides having Formula III. In certain embodiments, the internal region comprises from about 10 to about 12 β-D-2'-deoxyribonucleosides and each external region independently comprises 2 bicyclic nucleosides having Formula III. In certain embodiments, the internal region comprises 10 β-D-2'-deoxyribonucleosides and each external region independently comprises 2 bicyclic nucleosides having Formula III. In certain embodiments, each external region independently comprises from 2 to about 3 bicyclic nucleosides having Formula III and the internal region comprises 14 β-D-2'-deoxyribonucleosides. In certain embodiments, each external region independently comprises 2 bicyclic nucleosides having Formula III and the internal region comprises 14 β-D-2'-deoxyribonucleosides.

In certain embodiments, gapped oligomeric compounds are provided each having an internal region of from about 6 to about 14 monomeric subunits separating two external regions independently comprising from 1 to about 5 contiguous bicyclic nucleosides having Formula IV:

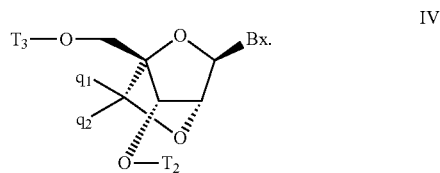

IV

In certain embodiments, oligomeric compounds comprising at least one bicyclic nucleoside having Formula III are provided comprising from about 8 to about 40 monomer subunits in length. In certain embodiments, oligomeric compounds comprising at least one bicyclic nucleoside having Formula III are provided comprising from about 8 to about 20 monomer subunits in length. In certain embodiments, oligomeric compounds comprising at least one bicyclic nucleoside having Formula III are provided comprising from about 10 to about 16 monomer subunits in length. In certain embodiments, oligomeric compounds comprising at least one bicyclic nucleoside having Formula III are provided comprising from about 10 to about 14 monomer subunits in length.

In certain embodiments, methods of inhibiting gene expression are provided comprising contacting one or more cells, a tissue or an animal with an oligomeric compound comprising at least one bicyclic nucleoside having Formula III.

In certain embodiments, methods are provided comprising contacting a cell with an oligomeric compound comprising at least one bicyclic nucleoside of Formula III:

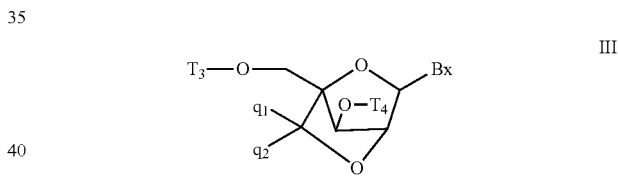

III wherein independently for each of said at least one bicyclic nucleoside having Formula III:

Bx is a heterocyclic base moiety;

$T_3$ and $T_4$ are each, independently, an internucleoside linking group linking the bicyclic nucleoside having Formula III to the oligomeric compound or one of $T_3$ and $T_4$ is an internucleoside linking group linking the bicyclic nucleoside having Formula III to the oligomeric compound and the other of $T_3$ and $T_4$ is H, a hydroxyl protecting group, a linked conjugate group or a 5' or 3'-terminal group;

$q_1$ and $q_2$ are each, independently, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_1$, $SJ_1$, $SOJ_1$, $SO_2J_1$, $NJ_1J_2$, $N_3$, CN, C(=O)$OJ_1$, C(=O)$NJ_1J_2$, C(=O)$J_1$, O—C(=O)$NJ_1J_2$, N(H)C(=NH)$NJ_1J_2$, N(H)C(=O)$NJ_1J_2$ or N(H)C(=S)$NJ_1J_2$;

or $q_1$ and $q_2$ together are =c($q_3$)($q_4$);

$q_3$ and $q_4$ are each, independently, H, halogen, $C_1$-$C_{12}$ alkyl or substituted $C_1$-$C_{12}$ alkyl;

each substituted group is, independently, mono or poly substituted with substituent groups independently selected from halogen, $C_1$-$C_6$ alkyl, $C_2$-$C_6$ alkenyl, $C_2$-$C_6$ alkynyl, $SJ_1$, $NJ_1J_2$, $N_3$, CN, C(=O)$OJ_1$, C(=O)$NJ_1J_2$, C(=O-0)$J_1$, O—C(=O)$NJ_1J_2$, N(H)C(=O)$NJ_1J_2$ or N(H)C(=S)$NJ_1J_2$;

each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group; and wherein said oligomeric compound comprises from about 8 to about 40 monomeric subunits and is complementary to a target RNA.

In certain embodiments, the cell is in an animal. In certain embodiments, the cell is in a human. In certain embodiments, the target RNA is selected from mRNA, pre-mRNA and micro RNA. In certain embodiments, the target RNA is mRNA. In certain embodiments, the target RNA is human mRNA. In certain embodiments, the target RNA is cleaved thereby inhibiting its function. In certain embodiments, the method further comprises evaluating the antisense activity of said oligomeric compound on said cell. In certain embodiments, the evaluating comprises detecting the levels of target RNA. In certain embodiments, the evaluating comprises detecting the levels of a protein. In certain embodiments, the evaluating comprises detection of one or more phenotypic effects.

In certain embodiments, bicyclic nucleosides are provided having the formula:

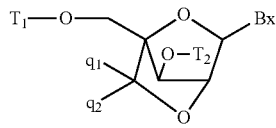

wherein:

Bx is a heterocyclic base moiety;

one of $T_1$ and $T_2$ is H or a hydroxyl protecting group and the other of $T_1$ and $T_2$ is H, a hydroxyl protecting group or a reactive phosphorus group;

$q_1$ and $q_2$ are each, independently, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_1$, $SJ_1$, $SOJ_1$, $SO_2J_1$, $NJ_1J_2$, $N_3$, CN, $C(=O)OJ_1$, $C(=O)NJ_1J_2$, $C(=O)J_1$, $O-C(=O)NJ_1J_2$, $N(H)C(=NH)NJ_1J_2$, $N(H)C(=O)NJ_1J_2$ or $N(H)C(=S)NJ_1J_2$;

or $q_1$ and $q_2$ together are $=C(q_3)(q_4)$;

$q_3$ and $q_4$ are each, independently, H, halogen, $C_1$-$C_{12}$ alkyl or substituted $C_1$-$C_{12}$ alkyl;

each $J_1$ and $J_2$ is, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ aminoalkyl, substituted $C_1$-$C_6$ aminoalkyl or a protecting group each $J_1$ and $J_2$ is, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ aminoalkyl, substituted $C_1$-$C_6$ aminoalkyl or a protecting group; and wherein each substituted group is, independently, mono or poly substituted with substituent groups independently selected from halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $OJ_1$, $SJ_1$, $NJ_1J_2$, $N_3$, CN, $C(=O)OJ_1$, $C(=O)NJ_1J_2$, $C(=O)J_1$, $O-C(=O)NJ_1J_2$, $N(H)C(=O)NJ_1J_2$ or $N(H)C(=S)NJ_1J_2$.

In one embodiment, at least one of $q_1$ and $q_2$ is $C_1$-$C_6$ alkyl or substituted $C_1$-$C_6$ alkyl. In another embodiment, both $q_1$ and $q_2$ are $C_1$-$C_6$ alkyl or substituted $C_1$-$C_6$ alkyl. In a further embodiment, both $q_1$ and $q_2$ are, independently, methyl. In another embodiment, at least one of $q_1$ and $q_2$ is substituted $C_1$-$C_6$ alkyl. In a further embodiment, at least one of $q_1$ and $q_2$ is $(CH_2)_n-N(H)C(=O)(CH_2)_n-NJ_1J_2$, $(CH_2)$, $-N(H)C(=S)NJ_1J_2$, $(CH_2)$, $-O-C(=O)NJ_1J_2$ or $C(=O)NJ_1J_2$ where a preferred n is 1.

Also provided herein are unsaturated substituents on the bridge wherein $q_1$ and $q_2$ together with the bonds that attach them to the 6-carbon atom of the bridge are $-C(q_3)(q_4)$. In one embodiment, $q_3$ and $q_4$ are each, independently, H. In another embodiment, at least one of $q_3$ and $q_4$ is halogen, $C_1$-$C_6$ alkyl or substituted $C_1$-$C_6$ alkyl. In a further embodiment, at least one of $q_3$ and $q_4$ is methyl. In another embodiment, both of $q_3$ and $q_4$ are, independently, methyl.

In one embodiment, each of $T_1$ and $T_2$ is a hydroxyl protecting group wherein preferred hydroxyl protecting groups include acetyl, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, benzoyl, p-phenylbenzoyl, 2,6-dichlorobenzyl, diphenylmethyl, p-nitrobenzyl, triphenylmethyl (trityl), 4,4'-dimethoxytrityl, trimethylsilyl, triethylsilyl, t-butyldimethylsilyl, t-butyldiphenylsilyl, triphenylsilyl, triisopropylsilyl, benzoylformate, chloroacetyl, trichloroacetyl, trifluoroacetyl, pivaloyl, 9-fluorenylmethyl carbonate, mesylate, tosylate, triflate, trityl, monomethoxytrityl, dimethoxytrityl, trimethoxytrityl, 9-phenylxanthine-9-yl (Pixyl) and 9-(p-methoxyphenyl)xanthine-9-yl (MOX).

In one embodiment, $T_1$ is acetyl, benzyl, t-butyldimethylsilyl, t-butyldiphenylsilyl or 4,4'-dimethoxytrityl where a preferred group is 4,4'-dimethoxytrityl. In certain embodiments, $T_1$ is 4,4'-dimethoxytrityl and $T_2$ is diisopropylcyanoethoxy phosphoramidite.

In one embodiment, $T_2$ is a reactive phosphorus group wherein preferred reactive phosphorus groups include diisopropylcyanoethoxy phosphoramidite and H-phosphonate.

In one embodiment, Bx is a pyrimidine, substituted pyrimidine, purine or substituted purine. In certain embodiments, Bx is uracil, 5-methyluracil, 5-methylcytosine, 5-thiazolo-uracil, 5-thiazolo-cytosine, adenine, guanine or 2,6-diaminopurine.

In one embodiment, each $J_1$ and $J_2$ is, independently, H or $C_1$-$C_3$ alkyl.

In one embodiment, the bicyclic nucleosides have the configuration:

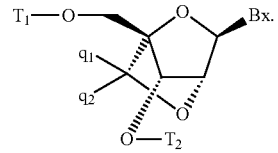

Oligomeric compounds are also provided having at least one bicyclic nucleoside having formula I:

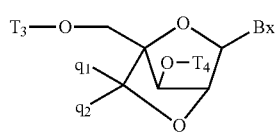

wherein:

Bx is a heterocyclic base moiety;

$T_3$ is hydroxyl, a protected hydroxyl, a linked conjugate group or an internucleoside linking group attached to a nucleoside, a nucleotide, an oligonucleoside, an oligonucleotide, a monomeric subunit or an oligomeric compound;

$T_4$ is hydroxyl, a protected hydroxyl, a linked conjugate group or an internucleoside linking group attached to a nucleoside, a nucleotide, an oligonucleoside, an oligonucleotide, a monomeric subunit or an oligomeric compound;

wherein at least one of $T_3$ and $T_4$ is an internucleoside linking group attached to a nucleoside, a nucleotide, an oligonucleoside, an oligonucleotide, a monomeric subunit or an oligomeric compound;

$q_1$ and $q_2$ are each, independently, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_1$, $SJ_1$, $SOJ_1$, $SO_2J_1$, $NJ_1J_2$, $N_3$, CN, C(=O)$OJ_1$, C(=O)$NJ_1J_2$, C(=O)$J_1$, O—C(=O)$NJ_1J_2$, N(H)C(=NH)$NJ_1J_2$, N(H)C(=O)$NJ_1J_2$ or N(H)C(=S)$NJ_1J_2$;

or $q_1$ and $q_2$ together are =C($q_3$)($q_4$);

$q_3$ and $q_4$ are each, independently, H, halogen, $C_1$-$C_{12}$ alkyl or substituted $C_1$-$C_{12}$ alkyl;

each $J_1$ and $J_2$ is, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ aminoalkyl, substituted $C_1$-$C_6$ aminoalkyl or a protecting group each $J_1$ and $J_2$ is, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ aminoalkyl, substituted $C_1$-$C_6$ aminoalkyl or a protecting group; and wherein each substituted group is, independently, mono or poly substituted with substituent groups independently selected from halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $OJ_1$, $SJ_1$, $NJ_1J_2$, $N_3$, CN, C(=O)$OJ_1$, C(=O)$NJ_1J_2$, C(=O)$J_1$, O—C(=O)$NJ_1J_2$, N(H)C(=O)$NJ_1J_2$ or N(H)C(=S)$NJ_1J_2$.

In one embodiment, at least one of $q_1$ and $q_2$ is $C_1$-$C_6$ alkyl or substituted $C_1$-$C_6$ alkyl. In another embodiment, both $q_1$ and $q_2$ are $C_1$-$C_6$ alkyl or substituted $C_1$-$C_6$ alkyl. In a further embodiment, both $q_1$ and $q_2$ are, independently, methyl. In another embodiment, at least one of $q_1$ and $q_1$ is substituted $C_1$-$C_6$ alkyl. In a further embodiment, at least one of $q_1$ and $q_2$ is $(CH_2)_n$—N(H)C(=O)$NJ_1J_2$, $(CH_2)_n$—N(H)C(=S)$NJ_1J_2$, $(CH_2)_n$—O—C(=O)$NJ_1J_2$ or $(CH_2)_n$—C(=O)$NJ_1J_2$ wherein a preferred n is 1.

Also provided are oligomeric compounds having at least one bicyclic nucleoside comprising an unsaturated substituent on the bridge wherein $q_1$ and $q_2$ together with the bonds that attach them to the 6-carbon atom of the bridge are =C($q_3$)($q_4$). In one embodiment, $q_3$ and $q_4$ are each, independently, H. In another embodiment, at least one of $q_3$ and $q_4$ is halogen, $C_1$-$C_6$ alkyl or substituted $C_1$-$C_6$ alkyl. In a further embodiment, at least one of $q_3$ and $q_4$ is methyl. In another embodiment, both of $q_3$ and $q_4$ are, independently, methyl.

In one embodiment, $T_3$ is H or a hydroxyl protecting group. In another embodiment $T_3$ is an internucleoside linking group attached to a nucleoside, a nucleotide or a monomeric subunit. In a further embodiment, $T_3$ is an internucleoside linking group attached to an oligonucleoside or an oligonucleotide. In another embodiment, $T_3$ is an internucleoside linking group attached to an oligomeric compound.

In one embodiment, $T_4$ is H or a hydroxyl protecting group. In another embodiment, $T_4$ is an internucleoside linking group attached to a nucleoside, a nucleotide or a monomeric subunit. In a further embodiment, $T_4$ is an internucleoside linking group attached to an oligonucleoside or an oligonucleotide. In another embodiment, $T_4$ is an internucleoside linking group attached to an oligomeric compound.

In one embodiment, at least one of $T_3$ and $T_4$ comprises an internucleoside linking group selected from phosphodiester or phosphorothioate.

In one embodiment, oligomeric compounds are provided having at least one bicyclic nucleoside having the configuration:

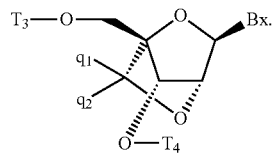

In one embodiment, oligomeric compounds having at least one bicyclic nucleoside of formula I are provided comprising a continuous sequence of linked nucleosides wherein each internucleoside linking group is, independently, a phosphodiester or a phosphorothioate.

In one embodiment, oligomeric compounds comprise at least one region of at least two contiguous bicyclic nucleosides having Formula I. In another embodiment, the region of at least two contiguous bicyclic nucleosides having Formula I located at the 3' or the 5'-end of the oligomeric compound. In a further embodiment, one region of at least two contiguous bicyclic nucleosides having Formula I is located at the 3' or the 5'-end of the oligomeric compound and at least one bicyclic nucleoside having Formula I located at the other of the 3' or the 5'-end of the oligomeric compound. In certain embodiments, gapped oligomeric compounds are provided having one region of at least two contiguous bicyclic nucleosides having formula I located at the 3' or the 5'-end and at least one bicyclic nucleoside having formula I located at the other of the 3' or the 5'-end of the oligomeric compound.

In certain embodiments, gapped oligomeric compounds are provided comprising one or two bicyclic nucleosides having Formula I at the 5'-end and two or three bicyclic nucleosides having Formula I at the 3'-end. In certain embodiments, gapped oligomeric compounds are provided comprising one or two bicyclic nucleosides having Formula I at the 5'-end, two or three bicyclic nucleosides having Formula I at the 3'-end and internal region of from about 10 to about 16 β-D-deoxyribonucleosides. In certain embodiments, the internal region of the gapped oligomeric compound comprises from about 10 to about 14 β-D-deoxyribonucleosides. In certain embodiments, gapped oligomeric compounds are provided comprising from 10 to 16 nucleosides and/or modified nucleosides or mimetics in length.

In one embodiment, oligomeric compounds are provided comprising from about 8 to about 40 nucleosides and/or modified nucleosides or mimetics in length. In another embodiment, oligomeric compounds are provided comprising from about 8 to about 20 nucleosides and/or modified nucleosides or mimetics in length. In a further embodiment, oligomeric compounds are provided comprising from about 10 to about 16 nucleosides and/or modified nucleosides or mimetics in length. In another embodiment, oligomeric compounds are provided comprising from about 10 to about 14 nucleosides and/or modified nucleosides or mimetics in length.

Also provided are methods of inhibiting gene expression comprising contacting one or more cells, a tissue or an animal with an oligomeric compound of the invention.

DETAILED DESCRIPTION OF THE INVENTION

Provided herein are 6-disubstituted bicyclic nucleosides, oligomeric compounds prepared therefrom and methods of using the oligomeric compounds. More particularly, each of the 6-disubstituted bicyclic nucleosides comprises a bridge between the 4' and 2'-positions of the ribose portion having one of the formulas: 2'-O—C($q_1$)($q_2$)-4' or 2'-O—C[=($q_3$)($q_4$)]-4'. In certain embodiments, the oligomeric compounds and compositions are designed to hybridize to a portion of a target RNA. In certain embodiments, the oligomeric compounds can be used in the design of aptamers which are oligomeric compounds capable of binding to aberrant proteins in an in vivo setting.

The 6-disubstituted bicyclic nucleosides are generally prepared having reactive groups orthogonally protected and further comprising a reactive phosphorus group. Such bicyclic nucleosides are useful as monomers subunits for oligomer synthesis. In certain embodiments, one illustrative example of such a monomer subunit as provided herein has the formula:

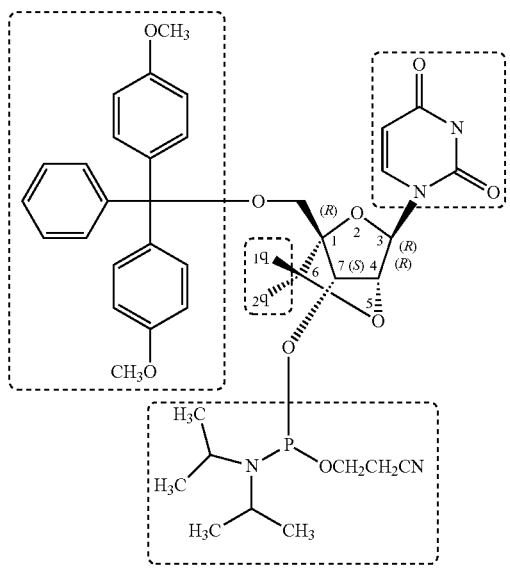

wherein the groups surrounded by broken lined boxes are variable. The bicyclic nucleoside monomer shown is generically referred to as a dimethoxytrityl phosphoramidite or more formally using IUPAC naming nomenclature as (1S,3R,4R,7S)-7-[2-cyanoethoxy(diisopropylamino)phosphinoxy]-1-(4,4'-dimethoxytrityloxymethyl)-3-(uracil-1-yl)-6-dimethyl-2,5-dioxa-bicyclo[2.2.1]heptane (when $q_1$ and $q_2$ are both methyl).

In certain embodiments, the 6-disubstituted bicyclic nucleosides provided herein are represented Formula Ia:

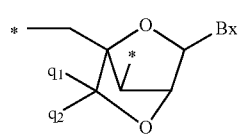

Ia where the asterisks are each, independently, a hydroxyl, a protected hydroxyl, an optionally linked conjugate group, a reporter group, a terminal group, a reactive phosphorus group, an internucleoside linkage connecting one or more nucleosides, or other group discussed herein or useful in antisense technology.

Bx is a heterocyclic base moiety;

$q_1$ and $q_2$ are each, independently, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_1$, $SJ_1$, $SOJ_1$, $SO_2J_1$, $NJ_1J_2$, $N_3$, CN, C(=O)$NJ_1J_2$, C(=O)$J_1$, O—C(=O)$NJ_1J_2$, N(H)C(=NH)$NJ_1J_2$, N(H)C(=O)$NJ_1J_2$ or N(H)C(=S)$NJ_1J_2$;

or $q_1$ and $q_2$ together are =C($q_3$)($q_4$);

$q_3$ and $q_4$ are each, independently, H, halogen, $C_1$-$C_{12}$ alkyl or substituted $C_1$-$C_{12}$ alkyl;

each substituted group is, independently, mono or poly substituted with substituent groups independently selected from halogen, $C_1$-$C_6$ alkyl, $C_2$-$C_6$ alkenyl, $C_2$-$C_6$ alkynyl, $OJ_1$, $SJ_1$, $NJ_1J_2$, $N_3$, CN, C(=O)$OJ_1$, C(=O)$NJ_1J_2$, C(=O)$J_1$, O—C(=O)$NJ_1J_2$, N(H)C(=O)$NJ_1J_2$ or N(H)C(=S)$NJ_1J_2$; and each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group.

In certain embodiments, 6-disubstituted bicyclic nucleosides are provided having Formula Ia and further having the configuration illustrated in Formula IIa:

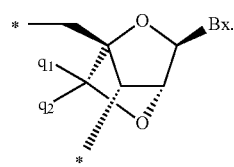

In certain embodiments, methods are provided wherein a cell is contacted with at least one of the oligomeric compounds provided herein, wherein the oligomeric compound is complementary to a target RNA. The cell may reside in an animal, preferably a human. The target RNA is selected from any RNA that would result in some benefit but preferably mRNA, pre-mRNA or micro RNA. In certain embodiments, the target RNA is cleaved as a result of interaction with the oligomeric compound thereby inhibiting its function. The efficiency of the methods provided herein can be evaluated by looking at a variety of criteria or end points such as evaluating the antisense activity by detecting the levels of a target RNA, detecting the level of a protein or by detecting one or more phenotypic effects.

The 6-disubstituted bicyclic nucleosides provided herein are useful for modifying oligomeric compounds at one or more positions. Such modified oligomeric compounds can be described as having a particular motif The term "motif" refers to the pattern of nucleosides in an oligomeric compound. The pattern is dictated by the positioning of nucleosides having unmodified (β-D-ribonucleosides and/or β-D-deoxyribonucleosides) and/or modified sugar groups within an oligomeric compound. The type of heterocyclic base and internucleoside linkages used at each position is variable and is not a factor in determining the motif of an oligomeric compound. The presense of one or more other groups including but not limited to capping groups and conjugate groups is also not a factor in determining the motif.

Certain motifs that can be prepared using the modified nucleosides provided herein include but are not limited to a gapped motif, a hemimer motif, a blockmer motif, a fully modified motif, a positionally modified motif and an alternating motif. In conjunction with these motifs a wide variety of internucleoside linkages can also be used including but not limited to phosphodiester and phosphorothioate linkages used uniformly or in combination. The positioning of the modified nucleosides provided herein and the use of linkage strategies can be easily optimized to maximize the activity of an oligomeric compound against a selected target.

Representative U.S. patents that teach the preparation of representative motifs include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety. Motifs are also disclosed in International Applications PCT/US2005/019219, filed Jun. 2, 2005 and published as WO 2005/121371 on Dec. 22, 2005 and PCT/US2005/019220, filed Jun. 2, 2005 and published as WO 2005/121372 on Dec. 22, 2005; each of which is incorporated by reference herein in its entirety.

As used herein term "gapmer" or "gapped oligomeric compound" refers to an oligomeric compound comprising a contiguous sequence of nucleosides having 3 regions, an internal region having an external region on each of the 5' and 3' ends. The internal region is differentiated from the external regions by having different sugar groups. The types of nucleosides that are generally used to differentiate the regions of a gapped oligomeric compound include β-D-ribonucleosides, β-D-2'-deoxyribonucleosides, 2'-modified nucleosides, 4'-thio modified nucleosides, 4'-thio-2'-modified nucleosides, and bicyclic sugar modified nucleosides. Each of the regions of a gapped oligomeric compound is essentially uniformly modified e.g. the sugar groups are identical with at least the internal region having different sugar groups than each of the external regions. The internal region (the gap) generally comprises β-D-deoxyribonucleosides but can be a sequence of sugar modified nucleosides. A preferred gapped oligomeric compound, as provided herein comprises an internal region of 3-D-deoxyribonucleosides with each of the external regions comprising bicyclic nucleosides having Formula III.

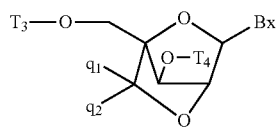

III

In certain embodiments, each of the regions of a gapped oligomeric compound are essentially uniformly modified e.g. the sugar groups are essentially identical with the internal region having different sugar groups than each of the external regions. The internal region or the gap generally comprises β-D-deoxyribonucleosides but can be a sequence of sugar modified nucleosides. In certain embodiments, the gapped oligomeric compounds comprise an internal region of β-D-deoxyribonucleosides with both of the external regions comprising modified nucleosides. Examples of gapped oligomeric compounds are illustrated in the example section.

In certain embodiments, gapped oligomeric compounds are provided comprising one or two bicyclic nucleosides having Formula I at the 5'-end, two or three bicyclic nucleosides having Formula I at the 3'-end and an internal region of from 10 to 16 nucleosides. In certain embodiments, gapped oligomeric compounds are provided comprising one bicyclic nucleosides having formula I at the 5'-end, two bicyclic nucleosides having formula I at the 3'-end and an internal region of from 10 to 16 nucleosides. In certain embodiments, gapped oligomeric compounds are provided comprising one bicyclic nucleosides having Formula I at the 5'-end, two bicyclic nucleosides having Formula I at the 3'-end and an internal region of from 10 to 14 nucleosides. In certain embodiments, the internal region is essentially a contiguous sequence of β-D-deoxyribonucleosides. In another embodiment, oligomeric compounds are provided that further include one or more terminal groups that include but are not limited to further modified or unmodified nucleosides or linked conjugate groups.

In certain embodiments, gapped oligomeric compounds are provided that are from about 10 to about 21 nucleosides in length. In another embodiment, gapped oligomeric compounds are provided that are from about 12 to about 16 nucleosides in length. In certain embodiments, gapped oligomeric compounds are provided that are from about 12 to about 14 nucleosides in length.

The terms "substituent" and "substituent group," as used herein, are meant to include groups that are typically added to other groups or parent compounds to enhance desired properties or give desired effects. Substituent groups can be protected or unprotected and can be added to one available site or to many available sites in a parent compound. Substituent groups may also be further substituted with other substituent groups and may be attached directly or via a linking group such as an alkyl or hydrocarbyl group to a parent compound. Such groups include without limitation, halogen, hydroxyl, alkyl, alkenyl, alkynyl, acyl (—C(O)$R_{aa}$), carboxyl (—C(O)O—$R_{aa}$), aliphatic groups, alicyclic groups, alkoxy, substituted oxy (—O—$R_{aa}$), aryl, aralkyl, heterocyclic, heteroaryl, heteroarylalkyl, amino (—$NR_{bb}R_{cc}$), imino(=$NR_{bb}$), amido (—C(O)N—$R_{bb}R_{cc}$ or —N($R_{bb}$)C(O)$R_{aa}$), azido (—$N_3$), nitro (—$NO_2$), cyano (—CN), carbamido (—OC(O)$NR_{bb}R_{cc}$ or —N($R_{bb}$)C(O)O$R_{aa}$), ureido (—N($R_{bb}$)C(O)$NR_{bb}R_{cc}$), thioureido (—N($R_{bb}$)C(S)$NR_{bb}R_{cc}$), guanidinyl (—N($R_{bb}$)C(—$NR_{bb}$)$NR_{bb}R_{cc}$), amidinyl (—C(—$NR_{bb}$)$NR_{bb}R_{cc}$ or —N($R_{bb}$)C($NR_{bb}$)$R_{aa}$), thiol (—$SR_{bb}$), sulfinyl (—S(O)$R_{bb}$), sulfonyl (—S(O)$_2R_{bb}$), sulfonamidyl (—S(O)$_2NR_{bb}R_{cc}$ or —N($R_{bb}$)—S(O)$_2R_{bb}$) and conjugate groups. Wherein each $R_{aa}$, $R_{bb}$ and $R_{cc}$ is, independently, H, an optionally linked chemical functional group or a further substituent group with a preferred list including, without limitation H, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

In this context, "recursive substituent" means that a substituent may recite another instance of itself. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by way of example and not limitation, physical properties such as molecular weight, solubility or log P, application properties such as activity against the intended target, and practical properties such as ease of synthesis.

Recursive substituents are an intended aspect of the invention. One of ordinary skill in the art of medicinal and organic chemistry understands the versatility of such substituents. To the degree that recursive substituents are present in a claim of the invention, the total number will be determined as set forth above.

The term "acyl," as used herein, refers to a radical formed by removal of a hydroxyl group from an organic acid and has the general formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substitutent groups.

The term "alicyclic" or "alicyclyl" refers to a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substitutent groups.

The term "aliphatic," as used herein, refers to a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation polyalkoxys, such as polyalkylene glycols, polyamines, and polyimines. Aliphatic groups as used herein may optionally include further substitutent groups.

The term "alkoxy," as used herein, refers to a radical formed between an alkyl group and an oxygen atom wherein the oxygen atom is used to attach the alkoxy group to a parent molecule. Examples of alkoxy groups include, but are not limited to, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substitutent groups.

The term "alkyl," as used herein, refers to a saturated straight or branched hydrocarbon radical containing up to twenty four carbon atoms. Examples of alkyl groups include, but are not limited to, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred. The term "lower alkyl" as used herein includes from 1 to about 6 carbon atoms. Alkyl groups as used herein may optionally include one or more further substitutent groups.

The term "alkenyl," as used herein, refers to a straight or branched hydrocarbon chain radical containing up to twenty four carbon atoms and having at least one carbon-carbon double bond. Examples of alkenyl groups include, but are not limited to, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substitutent groups.

The term "alkynyl," as used herein, refers to a straight or branched hydrocarbon radical containing up to twenty four carbon atoms and having at least one carbon-carbon triple bond. Examples of alkynyl groups include, but are not limited to, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substitutent groups.

The term "aminoalkyl" as used herein, refers to an amino substituted alkyl radical. This term is meant to include $C_1$-$C_{12}$ alkyl groups having an amino substituent at any position and wherein the alkyl group attaches the aminoalkyl group to the parent molecule. The alkyl and/or amino portions of the aminoalkyl group can be further substituted with substituent groups.

The terms "aralkyl" and "arylalkyl," as used herein, refer to a radical formed between an alkyl group and an aryl group wherein the alkyl group is used to attach the aralkyl group to a parent molecule. Examples include, but are not limited to, benzyl, phenethyl and the like. Aralkyl groups as used herein may optionally include further substitutent groups attached to the alkyl, the aryl or both groups that form the radical group.

The terms "aryl" and "aromatic," as used herein, refer to a mono- or polycyclic carbocyclic ring system radicals having one or more aromatic rings. Examples of aryl groups include, but are not limited to, phenyl, naphthyl, tetrahydronaphthyl, indanyl, idenyl and the like. Preferred aryl ring systems have from about 5 to about 20 carbon atoms in one or more rings. Aryl groups as used herein may optionally include further substitutent groups. The terms "halo" and "halogen," as used herein, refer to an atom selected from fluorine, chlorine, bromine and iodine.

The term "haloalkyl," as used herein, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. The term "perhaloalkyl," as used herein, refers to an alkyl group where all of the hydrogen atoms are replaced by halogen atoms. "Haloalkylene" refers to a haloalkyl group attached at two or more positions. Examples include floromethylene (—CFH—), difluoromethylene (—$CF_2$—), chloromethylene (—CHCl—) and the like.

The terms "heteroaryl," and "heteroaromatic," as used herein, refer to a radical comprising a mono- or poly-cyclic aromatic ring, ring system or fused ring system wherein at least one of the rings is aromatic and includes one or more heteroatom. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include, but are not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. Heteroaryl radicals can be attached to a parent molecule directly or through a linking moiety such as an aliphatic group or hetero atom. Heteroaryl groups as used herein may optionally include further substitutent groups.

The term "heteroarylalkyl," as used herein, refers to a heteroaryl group as previously defined having an alkyl radical that can attach the heteroarylalkyl group to a parent molecule. Examples include, but are not limited to, pyridinylmethyl, pyrimidinylethyl, napthyridinylpropyl and the like. Heteroarylalkyl groups as used herein may optionally include further substitutent groups on one or both of the heteroaryl or alkyl portions.

The term "heterocyclic radical" as used herein, refers to a radical mono-, or poly-cyclic ring system that includes at least one heteroatom and is unsaturated, partially saturated or fully saturated, thereby including heteroaryl groups. Heterocyclic is also meant to include fused ring systems wherein one or more of the fused rings contain at least one heteroatom and the other rings can contain one or more heteroatoms or optionally contain no heteroatoms. A heterocyclic group typically includes at least one atom selected from sulfur, nitrogen or oxygen. Examples of heterocyclic groups include, [1,3] dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, tetrahydrofuryl and the like. Heterocyclic groups as used herein may optionally include further substituent groups.

The term "hydrocarbyl" includes groups comprising C, O and H. Included are straight, branched and cyclic groups having any degree of saturation. Such hydrocarbyl groups can include one or more heteroatoms selected from N, O and S and can be further mono or poly substituted with one or more substituent groups.

The term "mono or poly cyclic structure" as used herein includes all ring systems that are single or polycyclic having rings that are fused or linked and is meant to be inclusive of single and mixed ring systems individually selected from aliphatic, alicyclic, aryl, heteroaryl, aralkyl, arylalkyl, heterocyclic, heteroaryl, heteroaromatic, heteroarylalkyl. Such mono and poly cyclic structures can contain rings that are uniform or have varying degrees of saturation including fully saturated, partially saturated or fully unsaturated. Each ring can comprise ring atoms selected from C, N, O and S to give rise to heterocyclic rings as well as rings comprising only C ring atoms which can be present in a mixed motif such as for example benzimidazole wherein one ring has only carbon ring atoms and the fused ring has two nitrogen atoms. The mono or poly cyclic structures can be further substituted with substituent groups such as for example phthalimide which has two $=O$ groups attached to one of the rings. In another aspect, mono or poly cyclic structures can be attached to a parent molecule directly through a ring atom, through a substituent group or a bifunctional linking moiety.

The term "oxo" refers to the group ($=O$).

The term "bicyclic nucleic acid", "BNA", "bicyclic nucleoside" or "bicyclic nucleotide" refers to a nucleoside or nucleotide wherein the furanose portion of the nucleoside includes a bridge connecting two carbon atoms on the furanose ring, thereby forming a bicyclic ring system.

The term "chimeric oligomeric compound" or "chimeric oligonucleotide" refers to an oligomeric compound or an oligonucleotide having at least one sugar, nucleobase or internucleoside linkage that is modified relative to naturally occurring linked nucleosides. The remainder of the sugars, nucleobases and internucleoside linkages can be independently modified or unmodified wherein each nucleoside and linkage can be the same or different.

The terms "stable compound" and "stable structure" are meant to indicate a compound that is sufficiently robust to survive isolation to a useful degree of purity from a reaction mixture, and formulation into an efficacious therapeutic agent. Only stable compounds are contemplated herein.

Linking groups or bifunctional linking moieties such as those known in the art can be used with the oligomeric compounds provided herein. Linking groups are useful for attachment of chemical functional groups, conjugate groups, reporter groups and other groups to selective sites in a parent compound such as for example an oligomeric compound. In general a bifunctional linking moiety comprises a hydrocarbyl moiety having two functional groups. One of the functional groups is selected to bind to a parent molecule or compound of interest and the other is selected to bind essentially any selected group such as a chemical functional group or a conjugate group. In certain embodiments, the linker comprises a chain structure or an oligomer of repeating units such as ethylene glycol or amino acid units. Examples of functional groups that are routinely used in bifunctional linking moieties include, but are not limited to, electrophiles for reacting with nucleophilic groups and nucleophiles for reacting with electrophilic groups. In certain embodiments, bifunctional linking moieties include amino, hydroxyl, carboxylic acid, thiol, unsaturations (e.g., double or triple bonds), and the like. Some nonlimiting examples of bifunctional linking moieties include 8-amino-3,6-dioxaoctanoic acid (ADO), succinimidyl 4-(N-maleimidomethyl)cyclohexane-1-carboxylate (SMCC) and 6-aminohexanoic acid (AHEX or AHA). Other linking groups include, but are not limited to, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, oligomeric compounds are modified by covalent attachment of one or more 5' or 3'-terminal groups. The term "terminal group" as used herein is meant to include useful groups known to the art skilled that can be placed on one or both of the 3' and 5'-ends of an oligomeric compound for various purposes such as enabling the tracking of the oligomeric compound (a fluorescent label or other reporter group), improving the pharmacokinetics or pharmacodynamics of the oligomeric compound (a group for enhancing uptake and delivery) or enhancing one or more other desirable properties of the oligomeric compound (group for improving nuclease stability or binding affinity). In certain embodiments, 3' and 5'-terminal groups include without limitation, one or more modified or unmodified nucleosides, conjugate groups, capping groups, phosphate moieties and protecting groups.

In certain embodiments, oligomeric compounds are modified by covalent attachment of one or more conjugate groups. In general, conjugate groups modify one or more properties of the attached oligomeric compound including but not limited to pharmacodynamic, pharmacokinetic, binding, absorption, cellular distribution, cellular uptake, charge and clearance. Conjugate groups are routinely used in the chemical arts and are linked directly or via an optional linking moiety or linking group to a parent compound such as an oligomeric compound. A preferred list of conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes.

The term "protecting group," as used herein, refers to a labile chemical moiety which is known in the art to protect reactive groups including without limitation, hydroxyl, amino and thiol groups, against undesired reactions during synthetic procedures. Protecting groups are typically used selectively and/or orthogonally to protect sites during reactions at other reactive sites and can then be removed to leave the unprotected group as is or available for further reactions. Protecting groups as known in the art are described generally in Greene and Wuts, Protective Groups in Organic Synthesis, 3rd edition, John Wiley & Sons, New York (1999).

Groups can be selectively incorporated into oligomeric compounds of the invention as precursors. For example an amino group can be placed into a compound of the invention as an azido group that can be chemically converted to the amino group at a desired point in the synthesis. Generally, groups are protected or present as precursors that will be inert to reactions that modify other areas of the parent molecule for conversion into their final groups at an appropriate time. Further representative protecting or precursor groups are discussed in Agrawal, et al., Protocols for Oligonucleotide Conjugates, Eds, Humana Press; New Jersey, 1994; Vol. 26 pp. 1-72.

Examples of hydroxyl protecting groups include, but are not limited to, acetyl, t-butyl, t-butoxymethyl, methoxymethyl, tetrahydropyranyl, 1-ethoxyethyl, 1-(2-chloroethoxy) ethyl, p-chlorophenyl, 2,4-dinitrophenyl, benzyl, 2,6-dichlorobenzyl, diphenylmethyl, p-nitrobenzyl, bis(2-acetoxyethoxy)methyl (ACE), 2-trimethylsilylethyl, trimethylsilyl, triethylsilyl, t-butyldimethylsilyl, t-butyldiphenylsilyl, triphenylsilyl, [(triisopropylsilyl)oxy]methyl (TOM), benzoylformate, chloroacetyl, trichloroacetyl, trifluoroacetyl, pivaloyl, benzoyl, p-phenylbenzoyl, 9-fluorenylmethyl carbonate, mesylate, tosylate, triphenylmethyl (trityl), monomethoxytrityl, dimethoxytrityl (DMT), trimethoxytrityl, 1(2-fluorophenyl)-4-methoxypiperidin-4-yl (FPMP) and substituted pixyl. Where more preferred hydroxyl protecting groups include, but are not limited to, benzyl, 2,6-dichlorobenzyl, t-butyldimethylsilyl, t-butyldiphenylsilyl, benzoyl, mesylate, tosylate, dimethoxytrityl (DMT) and substituted pixyl.

Examples of amino protecting groups include, but are not limited to, carbamate-protecting groups, such as 2-trimethylsilylethoxycarbonyl (Teoc), 1-methyl-1-(4-biphenylyl) ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide-protecting groups, such as formyl, acetyl, trihaloacetyl, benzoyl, and nitrophenylacetyl; sulfonamide-protecting groups, such as 2-nitrobenzenesulfonyl; and imine- and cyclic imide-protecting groups, such as phthalimido and dithiasuccinoyl.

Examples of thiol protecting groups include, but are not limited to, triphenylmethyl (trityl), benzyl (Bn), and the like.

In certain embodiments, oligomeric compounds are prepared by connecting nucleosides with optionally protected phosphorus containing internucleoside linkages. Representative protecting groups for phosphorus containing internucleoside linkages such as phosphodiester and phosphorothioate linkages include β-cyanoethyl, diphenylsilylethyl, δ-cyanobutenyl, cyano p-xylyl (CPX), N-methyl-N-trifluoroacetyl ethyl (META), acetoxy phenoxy ethyl (APE) and butene-4-yl groups. See for example U.S. Pat. Nos. 4,725,677 and Re. 34,069 (β-cyanoethyl); Beaucage, S. L. and Iyer, R. P., Tetrahedron, 49 No. 10, pp. 1925-1963 (1993); Beaucage, S. L. and Iyer, R. P., Tetrahedron, 49 No. 46, pp. 10441-10488 (1993); Beaucage, S. L. and Iyer, R. P., Tetrahedron, 48 No. 12, pp. 2223-2311 (1992).

The term "orthogonally protected" refers to functional groups which are protected with different classes of protecting groups, wherein each class of protecting group can be removed in any order and in the presence of all other classes (see, Barany, G. and Merrifield, R. B., *J. Am. Chem. Soc.,* 1977, 99, 7363; idem, 1980, 102, 3084.) Orthogonal protection is widely used in for example automated oligonucleotide synthesis. A functional group is deblocked in the presence of one or more other protected functional groups which is not affected by the deblocking procedure. This deblocked functional group is reacted in some manner and at some point a further orthogonal protecting group is removed under a different set of reaction conditions. This allows for selective chemistry to arrive at a desired compound or oligomeric compound.

In certain embodiments, compounds having reactive phosphorus groups useful for forming internucleoside linkages are provided including for example phosphodiester and phosphorothioate internucleoside linkages. Such reactive phosphorus groups are known in the art and contain phosphorus atoms in $P^{III}$ or $P^V$ valence state including, but not limited to, phosphoramidite, H-phosphonate, phosphate triesters and phosphorus containing chiral auxiliaries. A preferred synthetic solid phase synthesis utilizes phosphoramidites ($P^{III}$ chemistry) as reactive phosphites. The intermediate phosphite compounds are subsequently oxidized to the $P^V$ state using known methods to yield, in certain embodiments, phosphodiester or phosphorothioate internucleotide linkages. Additional reactive phosphates and phosphites are disclosed in Tetrahedron Report Number 309 (Beaucage and Iyer, Tetrahedron, 1992, 48, 2223-2311).

As used herein the term "internucleoside linkage or internucleoside linking group" is meant to include all manner of internucleoside linking groups known in the art including but not limited to, phosphorus containing internucleoside linking groups such as phosphodiester and phosphorothioate, non-phosphorus containing internucleoside linking groups such as formacetyl and methyleneimino, and neutral non-ionic internucleoside linking groups such as amide-3 (3'-$CH_2$—C(=O)—N(H)-5'), amide-4 (3'-$CH_2$—N(H)—C(=O)-5').

Specific examples of oligomeric compounds useful in this invention include oligonucleotides containing modified e.g. non-naturally occurring internucleoside linkages. Two main classes of internucleoside linkages are defined by the presence or absence of a phosphorus atom. Modified internucleoside linkages having a phosphorus atom include, but are not limited to, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity can comprise a single 3' to 3' linkage at the 3'-most internucleotide linkage, i.e. a single inverted nucleoside residue which may be abasic (the nucleobase is missing or has a hydroxyl group in place thereof). Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Modified internucleoside linkages not having a phosphorus atom include, but are not limited to, those that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH$_2$ component parts. In the context of this invention, the term "oligonucleoside" refers to a sequence of two or more nucleosides that are joined by internucleoside linkages that do not have phosphorus atoms.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

Internucleoside linking groups also include neutral internucleoside linking groups which can include a phosphorus atom or not. As used herein the phrase "neutral internucleoside linkage" is intended to include internucleoside linkages that are non-ionic. Such neutral internucleoside linkages include but are not limited to phosphotriesters, methylphosphonates, MMI (3'-CH$_2$—N(CH$_3$)—O-5'), amide-3 (3'-CH$_2$—C(=O)—N(H)-5'), amide-4 (3'-CH$_2$—N(H)—C(=O)-5'), formacetal (3'-O—CH$_2$—O-5'), and thioformacetal (3'-S—CH$_2$—O-5'). Further neutral internucleoside linkages include nonionic linkages comprising siloxane (dialkylsiloxane), carboxylate ester, carboxamide, sulfide, sulfonate ester and amides (See for example: Carbohydrate Modifications in Antisense Research; Y. S. Sanghvi and P. D. Cook Eds. ACS Symposium Series 580; Chapters 3 and 4, (pp. 40-65)). Further neutral internucleoside linkages include nonionic linkages comprising mixed N, O, S and CH$_2$ component parts.

The compounds described herein contain one or more asymmetric centers and thus give rise to enantiomers, diastereomers, and other stereoisomeric forms that may be defined in terms of absolute stereochemistry, as (R)- or (S)-, α or β, or as (D)- or (L)- such as for amino acids and nucleosides. All such possible isomers, as well as their racemic and optically pure forms are applicable to the oligomeric compounds provided herein. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., Enantiomers, Racemates, and Resolutions (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

As used herein the term "oligomeric compound" refers to a polymer having at least a region that is capable of hybridizing to a nucleic acid molecule. The term "oligomeric compound" includes oligonucleotides, oligonucleotide analogs and oligonucleosides as well as nucleotide mimetics and/or mixed polymers comprising nucleic acid and non-nucleic acid components. The term "oligomeric compound" also includes polymers comprising linked monomeric subunits wherein the monomeric subunits include nucleosides, modified nucleosides, nucleoside analogs, nucleoside mimetics as well as non-nucleic acid components such as conjugate groups. In certain embodiments, mixtures of monomeric subunits such as but not limited to those listed provide oligomeric compounds having enhanced properties for uses such as therapeutics and diagnostics. The bicyclic nucleosides provided herein are classified as a modified nucleosides as the base and ribose sugar are still present. The monomeric subunits can be linked by naturally occurring phosphodiester internucleoside linkages or alternatively by any of a plurality of internucleoside linkages disclosed herein such as but not limited to phosphorothioate internucleoside linkages or mixtures thereof.

In general, an oligomeric compound comprises a backbone of linked monomeric subunits wherein each linked monomeric subunit is directly or indirectly attached to a heterocyclic base moiety. Oligomeric compounds may also include monomeric subunits that are not linked to a heterocyclic base moiety thereby providing abasic sites. The linkages joining the monomeric subunits, the sugar moieties or surrogates and the heterocyclic base moieties can be independently modified. The linkage-sugar unit, which may or may not include a heterocyclic base, may be substituted with a mimetic such as the monomers in peptide nucleic acids. The ability to modify or substitute portions or entire monomers at each position of an oligomeric compound gives rise to a large number of possible motifs.

Oligomeric compounds are routinely prepared linearly but can be joined or otherwise prepared to be circular and may also include branching. Oligomeric compounds can combined to form double stranded constructs such as for example two strands hybridized to form double stranded compositions. The double stranded compositions can be linked or separate and can include overhangs on the ends.

As is known in the art, a nucleoside is a base-sugar combination. The base portion of the nucleoside is normally a heterocyclic base moiety. The two most common classes of such heterocyclic bases are purines and pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. The respective ends of this linear polymeric structure can be joined to form a circular structure by hybridization or by formation of a covalent bond. However, open linear structures are generally desired. Within the oligonucleotide structure, the phosphate groups are commonly referred to as forming the internucleoside linkages of the oligonucleotide. The normal internucleoside linkage of RNA and DNA is a 3' to 5' phosphodiester linkage.

As used herein, the term "oligonucleotide" refers to an oligomer or polymer of ribonucleic acid (RNA) or deoxyribonucleic acid (DNA). This term includes oligonucleotides composed of naturally-occurring nucleobases, sugars and covalent internucleoside linkages. The term "oligonucleotide analog" refers to oligonucleotides that have one or more non-naturally occurring portions. Such non-naturally occurring oligonucleotides are often desired over naturally occurring forms because of desirable properties such as, for example, enhanced cellular uptake, enhanced affinity for nucleic acid target and increased stability in the presence of nucleases.

As used herein, the term "oligonucleoside" refers to a sequence of nucleosides that are joined by internucleoside linkages that do not have phosphorus atoms. Internucleoside linkages of this type include short chain alkyl, cycloalkyl, mixed heteroatom alkyl, mixed heteroatom cycloalkyl, one or more short chain heteroatomic and one or more short chain heterocyclic. These internucleoside linkages include, but are not limited to, siloxane, sulfide, sulfoxide, sulfone, acetyl, formacetyl, thioformacetyl, methylene formacetyl, thioformacetyl, alkenyl, sulfamate, methyleneimino, methylenehydrazino, sulfonate, sulfonamide, amide and others having mixed N, O, S and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

As used herein, the term "nucleobase" or "heterocyclic base moiety" is intended to by synonymous with "nucleic acid base or mimetic thereof." In general, a nucleobase is mono or polyheterocyclic moiety that is capable of hydrogen bonding to a base of a nucleic acid.

As used herein the term "unmodified nucleobase" or "natural nucleobase" includes the purine bases adenine (A) and guanine (G), and the pyrimidine bases thymine (T), cytosine (C) and uracil (U). As used herein the term "modified nucleobase" includes other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine(1H-pyrimido [5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deazaadenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993.

Modified nucleobases include, but are not limited to, universal bases, hydrophobic bases, promiscuous bases, size-expanded bases, and fluorinated bases as defined herein. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750, 692, which is commonly owned with the instant application and also herein incorporated by reference.

The oligomeric compounds provided herein may also comprise one or more nucleosides having modified sugar moieties. The furanosyl sugar ring can be modified in a number of ways including substitution with a substituent group (2', 3', 4' or 5'), bridging to form a BNA and substitution of the 4'-O with a heteroatom such as S or N(R). Some representative U.S. patents that teach the preparation of such modified sugars include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; 5,700,920; 6,600,032 and International Application PCT/US2005/ 019219, filed Jun. 2, 2005 and published as WO 2005/121371 on Dec. 22, 2005 certain of which are commonly owned with the instant application, and each of which is herein incorporated by reference in its entirety. A representative list of preferred modified sugars includes but is not limited to substituted sugars having a 2'-F, 2'-$OCH_2$ or a 2'—$O(CH_2)_2$—$OCH_3$ (2'-MOE or simply MOE) substituent group; 4'-thio modified sugars and bicyclic modified sugars.

As used herein the term "nucleoside mimetic" is intended to include those structures used to replace the sugar or the sugar and the base not the linkage at one or more positions of an oligomeric compound such as for example nucleoside mimetics having morpholino or bicyclo[3.1.0]hexyl sugar mimetics e.g. non furanose sugar units with a phosphodiester linkage. The term "sugar surrogate" overlaps with the slightly broader term "nucleoside mimetic" but is intended to indicate replacement of the sugar unit (furanose ring) only. The term "nucleotide mimetic" is intended to include those structures used to replace the nucleoside and the linkage at one or more positions of an oligomeric compound such as for example peptide nucleic acids or morpholinos (morpholinos linked by —N(H)—C(=O)—O— or other non-phosphodiester linkage).

In certain embodiments, the oligomeric compounds provided herein can comprise from about 8 to about 80 nucleosides and/or modified nucleosides or mimetics in length. One of ordinary skill in the art will appreciate that the invention embodies oligomeric compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleosides and/or modified nucleosides or mimetics in length, or any range therewithin.

In certain embodiments, the oligomeric compounds provided herein are 8 to 40 nucleosides and/or modified nucleosides or mimetics in length. One having ordinary skill in the art will appreciate that this embodies oligomeric compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleosides and/or modified nucleosides or mimetics in length, or any range therewithin.

In certain embodiments, the oligomeric compounds of the invention are 8 to 20 nucleosides and/or modified nucleosides or mimetics in length. One having ordinary skill in the art will appreciate that this embodies oligomeric compounds of 8, 9, 10, 11, 12, 13, 14, 15, 16, 17, 18, 19 or 20 nucleosides and/or modified nucleosides or mimetics in length, or any range therewithin.

In certain embodiments, the oligomeric compounds of the invention are 10 to 16 nucleosides and/or modified nucleosides or mimetics in length. One having ordinary skill in the art will appreciate that this embodies oligomeric compounds of 10, 11, 12, 13, 14, 15 or 16 nucleosides and/or modified nucleosides or mimetics in length, or any range therewithin.

In certain embodiments, the oligomeric compounds of the invention are 12 to 16 nucleosides and/or modified nucleosides or mimetics in length. One having ordinary skill in the art will appreciate that this embodies oligomeric compounds of 12, 13, 14, 15 or 16 nucleosides and/or modified nucleosides or mimetics in length, or any range therewithin.

In certain embodiments, the oligomeric compounds of the invention are 10 to 14 nucleosides and/or modified nucleosides or mimetics in length. One having ordinary skill in the art will appreciate that this embodies oligomeric compounds of 10, 11, 12, 13 or 14 nucleosides and/or modified nucleosides or mimetics in length, or any range therewithin.

In certain embodiments, the oligomeric compounds are provided having of any of a variety of ranges of lengths of linked monomer subunits. In certain embodiments, the invention provides oligomeric compounds consisting of X-Y linked monomer subunits, where X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X<Y. For example, in certain embodiments, the invention provides oligomeric compounds comprising: 8-9, 8-10, 8-11, 8-12, 8-13, 8-14, 8-15, 8-16, 8-17, 8-18, 8-19, 8-20, 8-21, 8-22, 8-23, 8-24, 8-25, 8-26, 8-27, 8-28, 8-29, 8-30, 9-10, 9-11, 9-12, 9-13, 9-14, 9-15, 9-16, 9-17, 9-18, 9-19, 9-20, 9-21, 9-22, 9-23, 9-24, 9-25, 9-26, 9-27, 9-28, 9-29, 9-30, 10-11, 10-12, 10-13, 10-14, 10-15, 10-16, 10-17, 10-18, 10-19, 10-20, 10-21, 10-22, 10-23, 10-24, 10-25, 10-26, 10-27, 10-28, 10-29, 10-30, 11-12, 11-13, 11-14, 11-15, 11-16, 11-17, 11-18, 11-19, 11-20, 11-21, 11-22, 11-23, 11-24, 11-25, 11-26, 11-27, 11-28, 11-29, 11-30, 12-13, 12-14, 12-15, 12-16, 12-17, 12-18, 12-19, 12-20, 12-21, 12-22, 12-23, 12-24, 12-25, 12-26, 12-27, 12-28, 12-29, 12-30, 13-14, 13-15, 13-16, 13-17, 13-18, 13-19, 13-20, 13-21, 13-22, 13-23, 13-24, 13-25, 13-26, 13-27, 13-28, 13-29, 13-30, 14-15, 14-16, 14-17, 14-18, 14-19, 14-20, 14-21, 14-22, 14-23, 14-24, 14-25, 14-26, 14-27, 14-28, 14-29, 14-30, 15-16, 15-17, 15-18, 15-19, 15-20, 15-21, 15-22, 15-23, 15-24, 15-25, 15-26, 15-27, 15-28, 15-29, 15-30, 16-17, 16-18, 16-19, 16-20, 16-21, 16-22, 16-23, 16-24, 16-25, 16-26, 16-27, 16-28, 16-29, 16-30, 17-18, 17-19, 17-20, 17-21, 17-22, 17-23, 17-24, 17-25, 17-26, 17-27, 17-28, 17-29, 17-30, 18-19, 18-20, 18-21, 18-22, 18-23, 18-24, 18-25, 18-26, 18-27, 18-28, 18-29, 18-30, 19-20, 19-21, 19-22, 19-23, 19-24, 19-25, 19-26, 19-29, 19-28, 19-29, 19-30, 20-21, 20-22, 20-23, 20-24, 20-25, 20-26, 20-27, 20-28, 20-29, 20-30, 21-22, 21-23, 21-24, 21-25, 21-26, 21-27, 21-28, 21-29, 21-30, 22-23, 22-24, 22-25, 22-26, 22-27, 22-28, 22-29, 22-30, 23-24, 23-25, 23-26, 23-27, 23-28, 23-29, 23-30, 24-25, 24-26, 24-27, 24-28, 24-29, 24-30, 25-26, 25-27, 25-28, 25-29, 25-30, 26-27, 26-28, 26-29, 26-30, 27-28, 27-29, 27-30, 28-29, 28-30, or 29-30 linked monomer subunits.

In certain embodiments, ranges for the length of the oligomeric compounds include 8-16, 8-20, 8-40, 10-12, 10-14, 10-16, 10-18, 10-20, 10-21, 12-14, 12-16, 12-18, 12-20 and 12-24 linked monomer subunits.

In certain embodiments, oligomerization of modified and unmodified nucleosides and mimetics thereof, can be performed according to literature procedures for DNA (Protocols for Oligonucleotides and Analogs, Ed. Agrawal (1993), Humana Press) and/or RNA (Scaringe, Methods (2001), 23, 206-217; Gait et al., Applications of Chemically synthesized RNA in RNA:Protein Interactions, Ed. Smith (1998), 1-36; Gallo et al., Tetrahedron (2001), 57, 5707-5713) synthesis as appropriate. Additional methods for solid-phase synthesis may be found in Caruthers U.S. Pat. Nos. 4,415,732; 4,458, 066; 4,500,707; 4,668,777; 4,973,679; and 5,132,418; and Koster U.S. Pat. Nos. 4,725,677 and Re. 34,069.

Commercially available equipment routinely used for the support medium based synthesis of oligomeric compounds and related compounds is sold by several vendors including, for example, Applied Biosystems (Foster City, Calif.). Any other means for such synthesis known in the art may additionally or alternatively be employed. Suitable solid phase techniques, including automated synthesis techniques, are described in F. Eckstein (ed.), Oligonucleotides and Analogues, a Practical Approach, Oxford University Press, New York (1991).

The synthesis of RNA and related analogs relative to the synthesis of DNA and related analogs has been increasing as efforts in RNAi increase. The primary RNA synthesis strategies that are presently being used commercially include 5'-O-DMT-2'-O-t-butyldimethylsilyl (TBDMS), 5'-O-DMT-2'-O-[1(2-fluorophenyl)-4-methoxypiperidin-4-yl] (FPMP), 2'-β-[(triisopropylsilyl)oxy]methyl (2'-O—CH$_2$—O—Si(iPr)$_3$ (TOM), and the 5'-O-silyl ether-2'-ACE (5'-O-bis(trimethylsiloxy)cyclododecyloxysilyl ether (DOD)-2'-O-bis(2-acetoxyethoxy)methyl (ACE). A current list of some of the major companies currently offering RNA products include Pierce Nucleic Acid Technologies, Dharmacon Research Inc., Amen Biotechnologies Inc., and Integrated DNA Technologies, Inc. One company, Princeton Separations, is marketing an RNA synthesis activator advertised to reduce coupling times especially with TOM and TBDMS chemistries.

The primary groups being used for commercial RNA synthesis are:

TBDMS=5'-O-DMT-2'-O-t-butyldimethylsilyl;
TOM=2'-O-[(triisopropylsilyl)oxy]methyl;
DOD/ACE=(5'-O-bis(trimethylsiloxy)cyclododecyloxysilyl ether-2'-O-bis(2-acetoxyethoxy)methyl
FPMP=5'-O-DMT-2'-O-[1(2-fluorophenyl)-4-methoxypiperidin-4-yl].

In certain embodiments, the aforementioned RNA synthesis strategies and strategies that would be a hybrid of the above e.g. using a 5'-protecting group from one strategy with a 2'-O-protecting from another strategy are included as methods of making oligomers applicable herein.

In the context of this invention, "hybridization" means the pairing of complementary strands of oligomeric compounds. In certain embodiments, one mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances.

An oligomeric compound is specifically hybridizable when binding of the compound to the target nucleic acid interferes with the normal function of the target nucleic acid to cause a loss of activity, and there is a sufficient degree of complementarity to avoid non-specific binding of the oligomeric compound to non-target nucleic acid sequences under conditions in which specific binding is desired, i.e., under physiological conditions in the case of in vivo assays or therapeutic treatment, and under conditions in which assays are performed in the case of in vitro assays.

"Complementary," as used herein, refers to the capacity for precise pairing of two nucleobases regardless of where the two are located. For example, if a nucleobase at a certain position of an oligomeric compound is capable of hydrogen bonding with a nucleobase at a certain position of a target nucleic acid, the target nucleic acid being a DNA, RNA, or oligonucleotide molecule, then the position of hydrogen bonding between the oligonucleotide and the target nucleic acid is considered to be a complementary position. The oligomeric compound and the further DNA, RNA, or oligonucleotide molecule are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligonucleotide and a target nucleic acid.

It is understood in the art that the sequence of an oligomeric compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure or hairpin structure). The oligomeric compounds provided herein can comprise at least about 70%, at least about 80%, at least about 90%, at least about 95%, or at least about 99% sequence complementarity to a target region within the target nucleic acid sequence to which they are targeted. For example, an oligomeric compound in which 18 of 20 nucleobases of the oligomeric compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an oligomeric compound which is 18 nucleobases in length having 4 (four) noncomplementary nucleobases which are flanked by two regions of complete complementarity with the target nucleic acid would have 77.8% overall complementarity with the target nucleic acid and would thus fall within the scope as disclosed herein. Percent complementarity of an oligomeric compound with a region of a target nucleic acid can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656).

Oligomeric compounds provided herein also include without limitation antisense oligomeric compounds, antisense oligonucleotides, ribozymes, external guide sequence (EGS) oligonucleotides, alternate splicers, primers, probes, and other oligomeric compounds which hybridize to at least a portion of the target nucleic acid. As such, these oligomeric compounds may be introduced in the form of single-stranded, double-stranded, circular or hairpin oligomeric compounds and may contain structural elements such as internal or terminal bulges or loops. Once introduced to a system, the oligomeric compounds of the invention may elicit the action of one or more enzymes or structural proteins to effect modification of the target nucleic acid.

One non-limiting example of such an enzyme is RNAse H, a cellular endonuclease which cleaves the RNA strand of an RNA:DNA duplex. It is known in the art that single-stranded oligomeric compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While one form of oligomeric compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

In certain embodiments, "suitable target segments" may be employed in a screen for additional oligomeric compounds that modulate the expression of a selected protein. "Modulators" are those oligomeric compounds that decrease or increase the expression of a nucleic acid molecule encoding a protein and which comprise at least an 8-nucleobase portion which is complementary to a suitable target segment. The screening method comprises the steps of contacting a suitable target segment of a nucleic acid molecule encoding a protein with one or more candidate modulators, and selecting for one or more candidate modulators which decrease or increase the expression of a nucleic acid molecule encoding a protein. In certain embodiments, once it is shown that the candidate modulator or modulators are capable of modulating (e.g. either decreasing or increasing) the expression of a nucleic acid molecule encoding a peptide, the modulator may then be employed in further investigative studies of the function of the peptide, or used as a research, diagnostic, or therapeutic agent.

In certain embodiments, suitable target segments may be combined with their respective complementary antisense oligomeric compounds to form stabilized double-stranded (duplexed) oligonucleotides. Such double stranded oligonucleotide moieties have been shown in the art to modulate target expression and regulate translation as well as RNA processing via an antisense mechanism. Moreover, the double-stranded moieties may be subject to chemical modifications (Fire et al., Nature, 1998, 391, 806-811; Timmons and Fire, Nature 1998, 395, 854; Timmons et al., Gene, 2001, 263, 103-112; Tabara et al., Science, 1998, 282, 430-431; Montgomery et al., Proc. Natl. Acad. Sci. USA, 1998, 95, 15502-15507; Tuschl et al., Genes Dev., 1999, 13, 3191-3197; Elbashir et al., Nature, 2001, 411, 494-498; Elbashir et al., Genes Dev. 2001, 15, 188-200). For example, such double-stranded moieties have been shown to inhibit the target by the classical hybridization of antisense strand of the duplex to the target, thereby triggering enzymatic degradation of the target (Tijsterman et al., Science, 2002, 295, 694-697).

In certain embodiments, the oligomeric compounds provided herein can also be applied in the areas of drug discovery and target validation. The oligomeric compounds can also be used in conjunction with the targets identified herein in drug discovery efforts to elucidate relationships that exist between proteins and a disease state, phenotype, or condition. These methods include detecting or modulating a target peptide comprising contacting a sample, tissue, cell, or organism with the oligomeric compounds, measuring the nucleic acid or protein level of the target and/or a related phenotypic or chemical endpoint at some time after treatment, and optionally comparing the measured value to a non-treated sample or sample treated with a further oligomeric compound of the invention. These methods can also be performed in parallel or in combination with other experiments to determine the function of unknown genes for the process of target validation or to determine the validity of a particular gene product as a target for treatment or prevention of a particular disease, condition, or phenotype.

As used herein, the term "dose" refers to a specified quantity of a pharmaceutical agent provided in a single administration. In certain embodiments, a dose may be administered in two or more boluses, tablets, or injections. For example, in certain embodiments, where subcutaneous administration is desired, the desired dose requires a volume not easily accommodated by a single injection. In such embodiments, two or more injections may be used to achieve the desired dose. In certain embodiments, a dose may be administered in two or more injections to minimize injection site reaction in an individual.

In certain embodiments, chemically-modified oligomeric compounds of the invention have a higher affinity for target RNAs than does non-modified DNA. In certain such embodiments, that higher affinity in turn provides increased potency allowing for the administration of lower doses of such compounds, reduced potential for toxicity and improvement in therapeutic index and decreased overall cost of therapy.

Effect of nucleoside modifications on RNAi activity is evaluated according to existing literature (Elbashir et al., Nature (2001), 411, 494-498; Nishikura et al., Cell (2001), 107, 415-416; and Bass et al., Cell (2000), 101, 235-238.)

The oligomeric compounds provided herein can be utilized for diagnostics, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway. The oligomeric compounds provided herein, either alone or in combination with other oligomeric compounds or therapeutics, can be used as tools in differential and/or combinatorial analyses to elucidate expression patterns of a portion or the entire complement of genes expressed within cells and tissues. Oligomeric compounds can also be effectively used as primers and probes under conditions favoring gene amplification or detection, respectively. These primers and probes are useful in methods requiring the specific detection of nucleic acid molecules encoding proteins and in the amplification of the nucleic acid molecules for detection or for use in further studies. Hybridization of the antisense oligonucleotides, particularly the primers and probes, of the invention with a nucleic acid can be detected by means known in the art. Such means may include conjugation of an enzyme to the oligonucleotide, radiolabelling of the oligonucleotide or any other suitable detection means. Kits using such detection means for detecting the level of selected proteins in a sample may also be prepared.

As one nonlimiting example, expression patterns within cells or tissues treated with one or more oligomeric compounds are compared to control cells or tissues not treated with oligomeric compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds and or oligomeric compounds which affect expression patterns.

Examples of methods of gene expression analysis known in the art include DNA arrays or microarrays (Brazma and Vilo, FEBS Lett., 2000, 480, 17-24; Celis, et al., FEBS Lett., 2000, 480, 2-16), SAGE (serial analysis of gene expression) (Madden, et al., Drug Discov. Today, 2000, 5, 415-425), READS (restriction enzyme amplification of digested cDNAs) (Prashar and Weissman, Methods Enzymol., 1999, 303, 258-72), TOGA (total gene expression analysis) (Sutcliffe, et al., Proc. Natl. Acad. Sci. U.S.A., 2000, 97, 1976-81), protein arrays and proteomics (Celis, et al., FEBS Lett., 2000, 480, 2-16; Jungblut, et al., Electrophoresis, 1999, 20, 2100-10), expressed sequence tag (EST) sequencing (Celis, et al., FEBS Lett., 2000, 480, 2-16; Larsson, et al., J. Biotechnol., 2000, 80, 143-57), subtractive RNA fingerprinting (SuRF) (Fuchs, et al., Anal. Biochem., 2000, 286, 91-98; Larson, et al., Cytometry, 2000, 41, 203-208), subtractive cloning, differential display (DD) (Jurecic and Belmont, Curr. Opin. Microbiol., 2000, 3, 316-21), comparative genomic hybridization (Carulli, et al., J. Cell Biochem. Suppl., 1998, 31, 286-96), FISH (fluorescent in situ hybridization) techniques (Going and Gusterson, Eur. J. Cancer, 1999, 35, 1895-904) and mass spectrometry methods (To, Comb. Chem. High Throughput Screen, 2000, 3, 235-41).

While the monomers, oligomers and methods provided herein have been described with specificity in accordance with certain of their embodiments, the following examples serve only to illustrate the invention and are not intended to limit the same.

EXAMPLE 1

Scheme 1

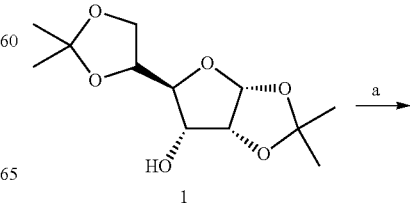

1

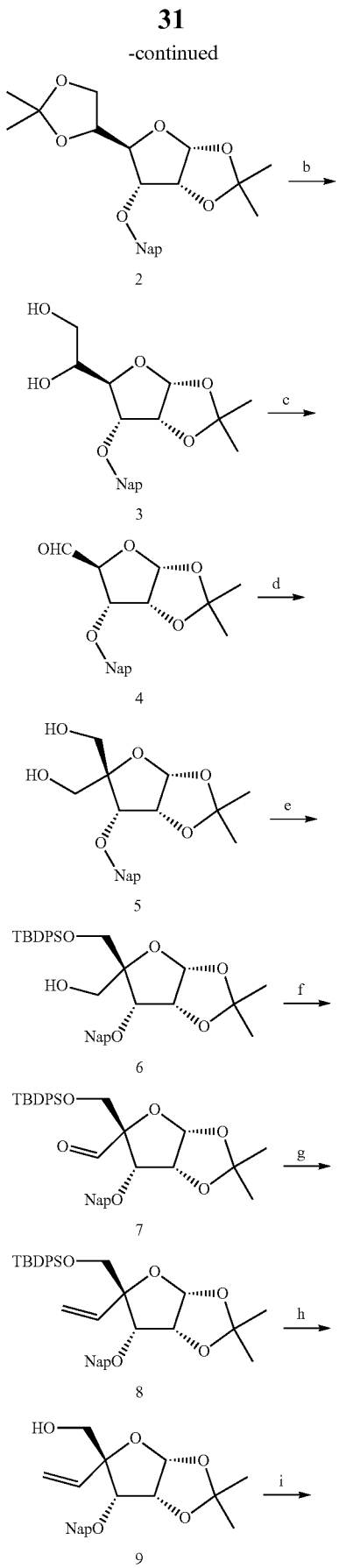

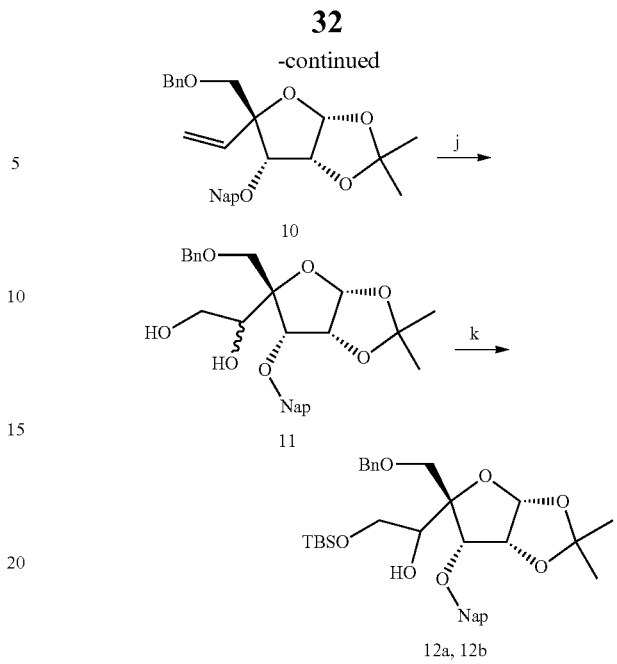

A) Compound 1

Sodium hydride (2.39 g, 59.8 mmol) was added carefully to a cold (0° C.) solution of commercially available 1,2:5,6-Di-O-isopropylidene-α-D-allofuranose, Compound 1 (12.0 g, 46 mmol) in DMF (75 mL). After stirring for 20 minutes, napthyl bromide (11.12 g, 50.8 mmol) was added to the reaction and the stirring was continued for another 2 hours. The reaction was carefully quenched with water and then poured into EtOAc and the organic layer was washed with water, brine, dried and concentrated. Purification by column chromatography ($SiO_2$, 10% to 33% EtOAc/hexanes) provided the alcohol, Compound 2 as a white solid (18.1 g, 98%).

B) Compound 5

Compound 2 (18 g, 46 mmol) was dissolved in glacial acetic acid (150 mL) and water (60 mL). The reaction was stirred at room temperature for 16 hours after which it was concentrated under vacuum. The residue was then dissolved in EtOAc and the organic layer was washed with saturated $NaHCO_3$, brine, dried and concentrated to provide crude Compound 3, which was used without any further purification.

A solution of sodium periodate (48 mmol, 10 g) in water (350 mL) was added to a solution of the Compound 3 obtained above, in 1,4-dioxane (140 mL). After stirring at room temperature for 90 minutes, the reaction was extracted with EtOAc and the organic layer was further washed with water, brine, dried ($Na_2SO_4$) and concentrated to provide the aldehyde, Compound 4, which was used without any further purification.

Crude Compound 4 from above, was dissolved in a mixture of THF:$H_2O$ (1:1, 100 mL) and the reaction was cooled in an ice bath. Formaldehyde (25 mL, 35% w/w) and 1 N NaOH (100 mL) were added to the reaction. After stirring at room temperature for 16 hours, formaldehyde (5 mL) was added to the reaction and stirring was continued for an additional 32 hours. The reaction was then concentrated to dryness and the residue was partitioned between EtOAc and water. The layers were separated and the organic layer was washed with additional 1N NaOH, water, brine, dried and concentrated to provide the diol, Compound 5 (12.96 g, 80%, three steps) as a white solid.

C) Compound 6 tert-Butyldiphenylsilyl chloride (0.75 mL, 2.9 mmol) was added to a cold (0° C.) solution of Compound 5 (1 g, 2.8 mmol) and triethylamine (0.45 mL, 3.2 mmol). After stirring at room temperature for 16 hours, the reaction was poured into EtOAc and sequentially washed with 5% HCl, saturated NaHCO$_3$, brine, dried (Na$_2$SO$_4$) and concentrated. Purification by column chromatography (SiO$_2$, eluting with 10% to 40% EtOAc/hexanes) provided the alcohol, Compound 6 (1.02 g, 61%) as an oil (0.42 g of the regioisomeric silyl protected diol was also isolated).

D) Compound 7

Dimethylsulfoxide (1.6 mL, 22.4 mmol) was added dropwise to a cold (−78° C.) solution of oxalyl chloride (0.98 mL, 11.2 mmol) in CH$_2$Cl$_2$ (70 mL). After stirring for 30 minutes, a solution of Compound 6 (4.8 g, 8.0 mmol) in CH$_2$Cl$_2$ (20 mL) was added to the reaction. The stirring was continued for 45 minutes at −78° C. and triethylamine (4.72 mL, 33.7 mmol) was added to the reaction. The reaction was stirred at −78° C. for 15 minutes after which the ice bath was removed and the reaction was allowed to gradually warm over 45 minutes. The reaction was then poured into CH$_2$Cl$_2$ and the organic phase was sequentially washed with 5% aqueous HCl, saturated NaHCO$_3$, brine, dried (Na$_2$SO$_4$) and concentrated under vacuum to provide the aldehyde, Compound 7, which was used without further purification.

E) Nucleoside 8 nBuLi (2.5 M, 4.34 mL, 10.9 mmol) was added dropwise to a cold (0° C.) stirring solution of triphenylphosphonium bromide (3.88 g, 10.9 mmol) in dry THF (60 mL). After stirring for 1 hour, the red solution was cooled to −78° C. and a solution of aldehyde 7 from above (8.4 mmol) in dry THF (15 mL) was added dropwise to the reaction. The reaction was gradually allowed to warm to room temperature and the stirring was continued for another 16 hours. The reaction was then carefully quenched using saturated NH$_4$Cl and partitioned between EtOAc and water. The organic layer was sequentially washed with brine, dried (Na$_2$SO$_4$) and concentrated. Purification by column chromatography (SiO$_2$, eluting with 10% EtOAc in hexanes) provided olefin, Compound 8 (4.84 g, 97% from 26) as a colorless oil.

F) Nucleoside 9

Tetrabutylammonium fluoride (1M in THF, 10.00 mL, 10.0 mmol) was added to a solution of Compound 8 (4.83 g, 8.1 mmol) in THF (35 mL). The reaction was stirred at room temperature for 16 hours after which the solvent was removed under vacuum and the residue was dissolved in EtOAc. The organic layer was washed with water, brine, dried (Na$_2$SO$_4$) and concentrated. Purification by column chromatography (SiO$_2$, eluting with 40% EtOAc in hexanes) provided alcohol, Compound 9 (2.79 g, 97%) as a colorless oil.

G) Nucleoside 10

Sodium hydride (60% w/w in mineral oil, 0.4 g, 10 mmol) was added to a cold (0° C.) solution of Compound 9 (1.44 g, 4.1 mmol) and benzyl bromide (0.71 mL, 6.0 mmol) in DMF (16 mL). After stirring for 1 hour at 0° C., the reaction was carefully quenched with water and partitioned between EtOAc and water. The organic layer was separated and washed with brine, dried (Na$_2$SO$_4$) and concentrated. Purification by column chromatography (SiO$_2$, eluting with 10 to 25% EtOAc in hexanes) provided olefin, Compound 10 (1.84 g, quantitative) as a colorless oil.

H) Nucleoside 11

Osmium Tetroxide (OsO$_4$, 25% solution in iPrOH, 1 mL) was added to a solution of Compound 10 (1.80 g, 4.0 mmol) and N-methylmorpholine-N-oxide (NMO, 0.94 g, 8.0 mmol) in 95% acetone/water (25 mL). After stirring for 16 h at room temperature, additional OsO$_4$ solution (0.5 mL) and NMO (0.40 g) were added to the reaction. After stirring for a total 48 hours, the reaction was diluted with EtOAc and washed with 10% NaHSO$_3$, brine, dried (Na$_2$SO$_4$) and concentrated. Purification by column chromatography (SiO$_2$, eluting with 40 to 50% EtOAc in hexanes) provided diol, Compound 11 (1.68 g, 87%, ca. 1:1 mixture of isomers) as a colorless oil.

I) Nucleosides 12a and 12b

TBSCl (0.66 g, 4.4 mmol) was added to a cold (0° C.) solution of Compound 11 (1.63 g, 3.4 mmol) in pyridine (17 mL). After stirring for 4 h at 0° C., the reaction was diluted with EtOAc and the organic layer was washed with water, brine, dried and concentrated. Purification by column chromatography (SiO$_2$, eluting with 10 to 20% EtOAc in hexanes) provided the alcohols, compounds 12a and 12b (0.90 g and 1.17 g, absolute stereochemistry not assigned) as colorless oils.

EXAMPLE 2

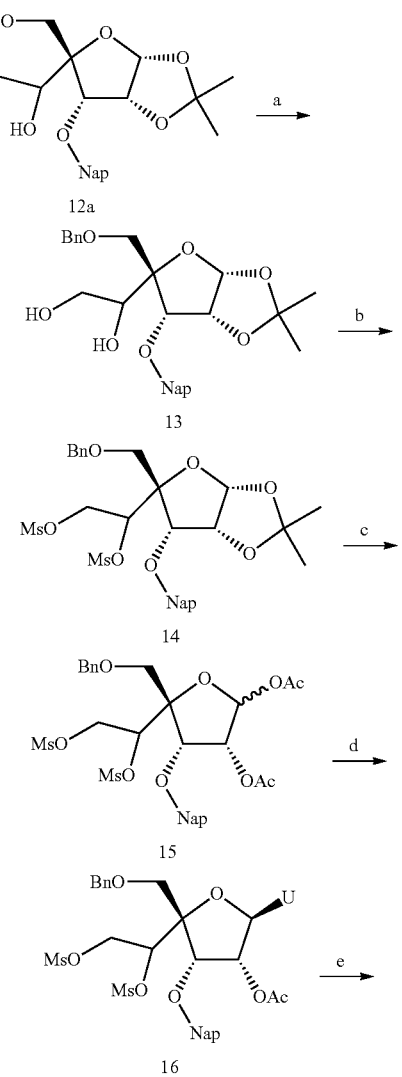

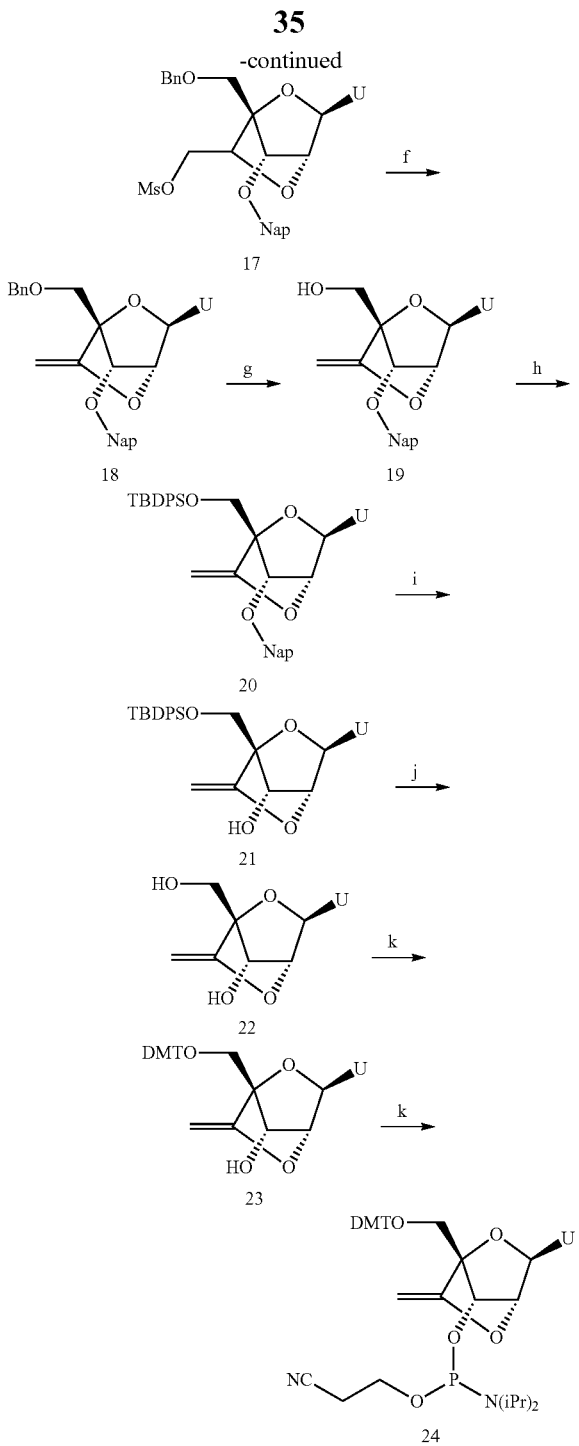

(a) Et$_3$N·3HF, Et$_3$N, THF, 84% (b) MsCl, Et$_3$N, DMAP, CH$_2$Cl$_2$, 79% (c) AcOH, Ac$_2$O, H$_2$SO$_4$, 44% (d) Uracil, BSA, TMSOTf, CH$_3$CN (e) K$_2$CO$_3$, MeOH, 51% from 154 (f) TBAF, THF, 80° C., 16h (g) BCl$_3$, CH$_2$Cl$_2$ (h) TBDPSCl, imidazole, DMF (i) DDQ, CH$_2$Cl$_2$, H$_2$O (j) Et$_3$N·3HF, Et$_3$N, THF (k) DMTCl, pyridine (l) (iPr$_2$N)$_2$POCH$_2$CH$_2$CN, tetrazole, NMI, DMF.

Compound 13

Triethylamine trihydrofluoride (1.56 mL, 9.6 mmol) was added to a solution of Compound 12a (0.95 g, 1.6 mmol, absolute stereochemistry of hydroxyl group not assigned) and triethylamine (0.56 mL, 4.0 mmol) in THF (16 mL). After stirring at room temperature for 16 hours, the THF was evaporated under vacuum and the residue was dissolved in EtOAc. The organic layer was washed with saturated NaHCO$_3$ solution, brine, dried (Na$_2$SO$_4$) and concentrated. Purification by column chromatography (SiO$_2$, eluting with 40 to 50% EtOAc in hexanes) provided the diol, Compound 13 (0.65 g, 84%).

Compound 14

Methanesulfonyl chloride (0.32 mL, 4.1 mmol) was added to a cold (0° C.) solution of Compound 13 (0.65 g, 1.4 mmol), triethylamine (0.57 mL, 4.1 mmol) and dimethylaminopyridine (49 mg, 0.4 mmol) in dichloromethane (4 mL). The reaction was gradually allowed to warm to room temperature and stirred 16 hours after which it was diluted with EtOAc. The organic layer was sequentially washed with 5% HCl, saturated NaHCO$_3$, brine, dried (Na$_2$SO$_4$) and concentrated. Purification by column chromatography (SiO$_2$, eluting with 40% EtOAc in hexanes) provided the dimesylate, Compound 14 (0.68 g, 79%).

Compound 154

Concentrated sulfuric acid (3 drops) was added to a solution of Compound 14 (0.68 g, 1.1 mmol), acetic acid (2 mL) and acetic anhydride (0.4 mL). After stirring at room temperature for 2 hours, the reaction was concentrated under high vacuum. The residue was diluted with EtOAc and carefully washed with saturated NaHCO$_3$ solution, brine, dried (Na$_2$SO$_4$) and concentrated. Purification by column chromatography (SiO$_2$, eluting with 40 to 50% EtOAc in hexanes) provided the diacetate, Compound 15 (0.32 g, 44%).

Compound 17

N,O-Bis(trimethylsilyl)acetamide (0.58 mL, 2.4 mmol) was added to a suspension of Compound 15 (0.32 g, 0.5 mmol) and uracil (0.11 g, 0.9 mmol) in CH$_3$CN (3 mL). After heating at 40° C. for 15 min to get a clear solution, trimethylsilyl triflate (0.13 mL, 0.7 mmol) was added to the reaction. After refluxing for 2 h, the reaction was cooled to room temperature and poured into EtOAc. The organic layer was washed with saturated NaHCO$_3$, brine, dried (Na$_2$SO$_4$) and concentrated under vacuum to provide the crude nucleoside, Compound 16, which was used without further purification.

K$_2$CO$_3$ (0.14 mg, 1.0 mmol) was added to a solution of the crude nucleoside, Compound 16 (from above) in MeOH (5 mL). After stirring for 16 h at room temperature, the solvent was removed under vacuum and the residue was partitioned between EtOAc and brine. The organic phase was collected, dried (Na$_2$SO$_4$) and concentrated under vacuum to provide 6 (absolute stereochemistry not determined). Purification by column chromatography (SiO$_2$, eluting with 25% acetone in CHCl$_3$) provided the nucleoside, Compound 17 (0.14 g, 51% from 4).

Compound 18

Tetrabutylammonium fluoride (1M solution in THF, 0.10 mL, 0.1 mmol) was added to a solution of Compound 17 in THF (0.05 mL). Heating the reaction at 100° C. for 16 hours provided the nucleoside, Compound 18. LCMS: retention time 3.81 min; M+H calcd. 499.18, found 499.0.

Compound 24

The benzyl protecting group in Compound 18 is removed using BCl$_3$ in dichloromethane at temperatures between −78° C. and 0° C. to provide Compound 19. The primary alcohol of Compound 19 is protected as the TBDPS ether to provide Compound 20. The 3'O-Nap protecting group is then removed using DDQ in dichloromethane and water to provide Compound 21. Removal of the 5'O-TBDPS protecting group provides Compound 22. The 5'-hydroxyl is protected using DMTCl in pyridine to provide Compound 23 which is phosphytilated to provide the amidite, Compound 24.

EXAMPLE 3
Scheme 3
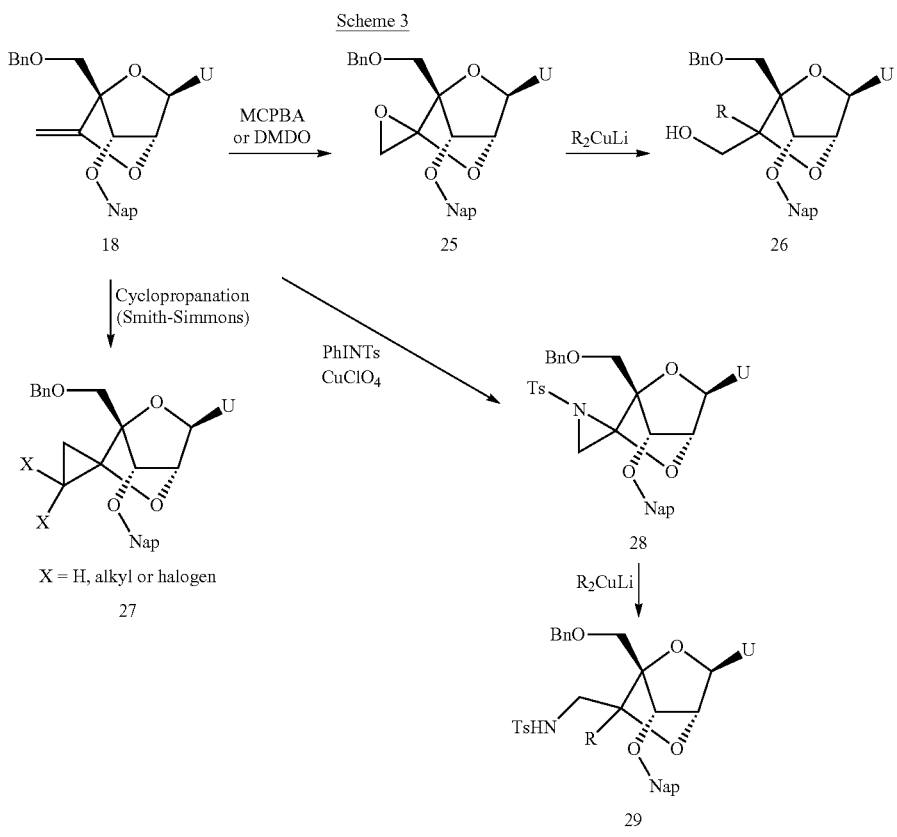
EXAMPLE 4
Scheme 4
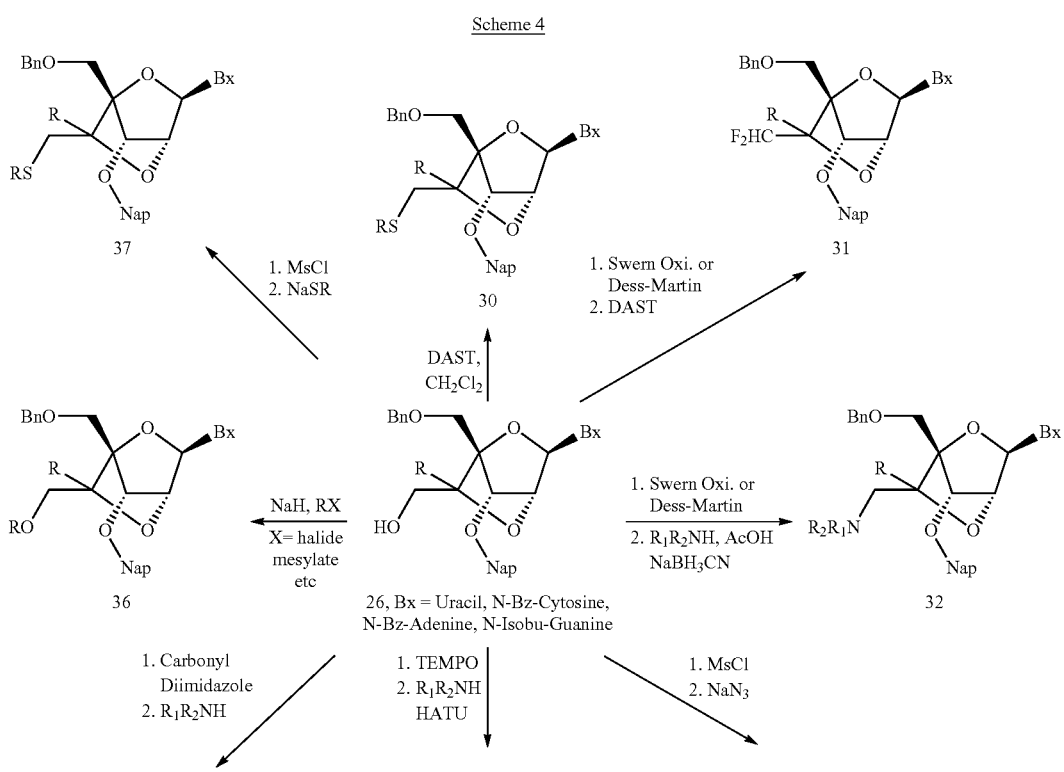

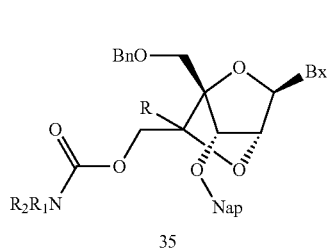
35

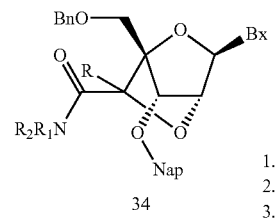
34

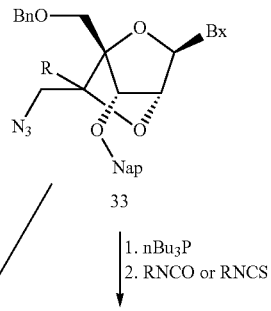
33

1. nBu₃P
2. FmocNCS
3. R₁R₂NH, EDC
4. Piperidine 1. nBu₃P
2. RNCO or RNCS

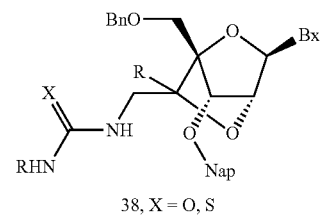
38, X = O, S

39

R, R₁ and R₂ are each independently H, halogen, alkyl, alkenyl, alkynyl, substituted alkyl, substituted alkenyl, substituted alkynyl, or a protecting group.

EXAMPLE 5

Scheme 5

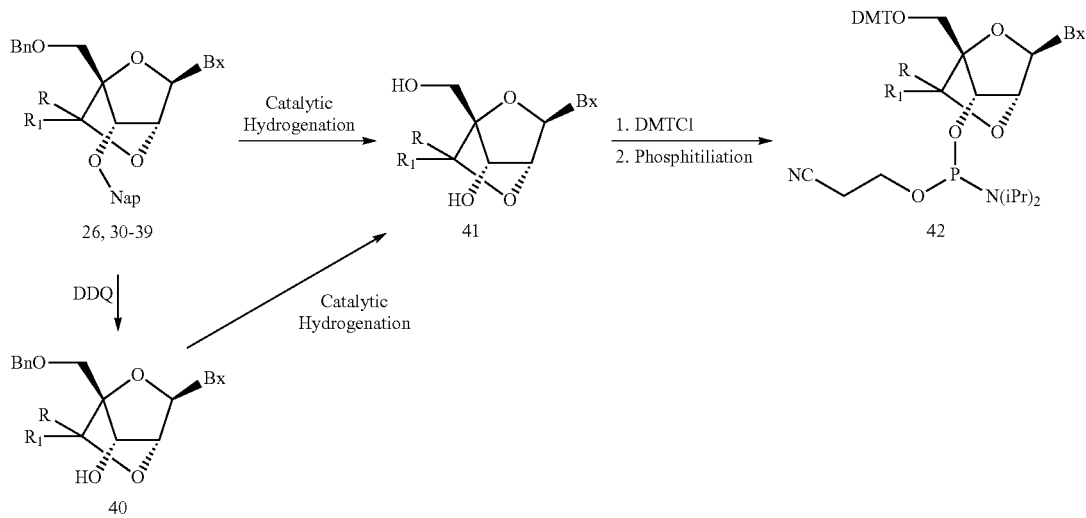

R and R₁ are each independently H, halogen, alkyl, alkenyl, alkynyl, substituted alkyl, substituted alkenyl, substituted alkynyl, or a protecting group.

EXAMPLE 6

Scheme 6

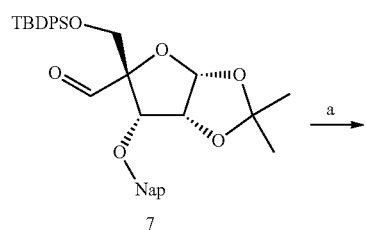
7

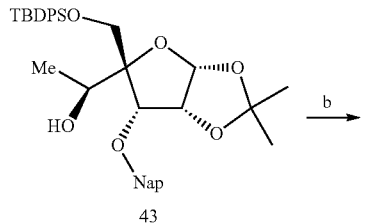
43

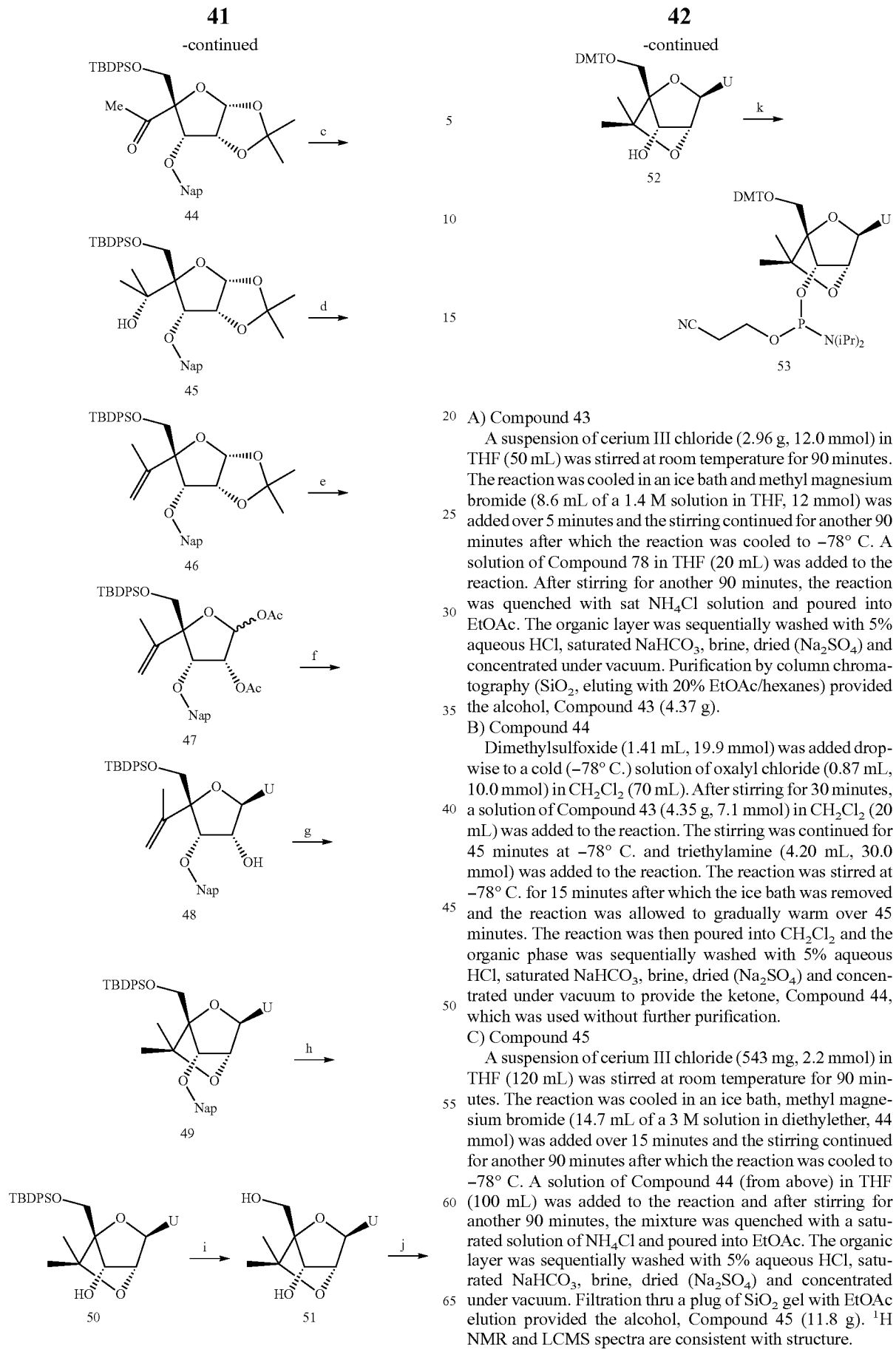

A) Compound 43

A suspension of cerium III chloride (2.96 g, 12.0 mmol) in THF (50 mL) was stirred at room temperature for 90 minutes. The reaction was cooled in an ice bath and methyl magnesium bromide (8.6 mL of a 1.4 M solution in THF, 12 mmol) was added over 5 minutes and the stirring continued for another 90 minutes after which the reaction was cooled to −78° C. A solution of Compound 78 in THF (20 mL) was added to the reaction. After stirring for another 90 minutes, the reaction was quenched with sat $NH_4Cl$ solution and poured into EtOAc. The organic layer was sequentially washed with 5% aqueous HCl, saturated $NaHCO_3$, brine, dried ($Na_2SO_4$) and concentrated under vacuum. Purification by column chromatography ($SiO_2$, eluting with 20% EtOAc/hexanes) provided the alcohol, Compound 43 (4.37 g).

B) Compound 44

Dimethylsulfoxide (1.41 mL, 19.9 mmol) was added dropwise to a cold (−78° C.) solution of oxalyl chloride (0.87 mL, 10.0 mmol) in $CH_2Cl_2$ (70 mL). After stirring for 30 minutes, a solution of Compound 43 (4.35 g, 7.1 mmol) in $CH_2Cl_2$ (20 mL) was added to the reaction. The stirring was continued for 45 minutes at −78° C. and triethylamine (4.20 mL, 30.0 mmol) was added to the reaction. The reaction was stirred at −78° C. for 15 minutes after which the ice bath was removed and the reaction was allowed to gradually warm over 45 minutes. The reaction was then poured into $CH_2Cl_2$ and the organic phase was sequentially washed with 5% aqueous HCl, saturated $NaHCO_3$, brine, dried ($Na_2SO_4$) and concentrated under vacuum to provide the ketone, Compound 44, which was used without further purification.

C) Compound 45

A suspension of cerium III chloride (543 mg, 2.2 mmol) in THF (120 mL) was stirred at room temperature for 90 minutes. The reaction was cooled in an ice bath, methyl magnesium bromide (14.7 mL of a 3 M solution in diethylether, 44 mmol) was added over 15 minutes and the stirring continued for another 90 minutes after which the reaction was cooled to −78° C. A solution of Compound 44 (from above) in THF (100 mL) was added to the reaction and after stirring for another 90 minutes, the mixture was quenched with a saturated solution of $NH_4Cl$ and poured into EtOAc. The organic layer was sequentially washed with 5% aqueous HCl, saturated $NaHCO_3$, brine, dried ($Na_2SO_4$) and concentrated under vacuum. Filtration thru a plug of $SiO_2$ gel with EtOAc elution provided the alcohol, Compound 45 (11.8 g). $^1H$ NMR and LCMS spectra are consistent with structure.

D) Compound 46

Compound 45 (11.8 g, 18.8 mmoles) was dissolved in pyridine (94 mL) and thionyl chloride (2.75 mL, 37.6 mmoles), and then heated at 60° C. for 1 hour. The reaction was cooled to room temperature and poured into EtOAc and brine. The organic layer was washed with brine, dried ($Na_2SO_4$) and concentrated under vacuum. Filtration thru a plug of $SiO_2$ and elution with EtOAc provided the alkene, Compound 46 (9.8 g). $^1$H NMR and LCMS spectra are consistent with structure.

E) Compound 47

Concentrated $H_2SO_4$ (2 drops) was added to a solution of Compound 46 (from above) in glacial acetic acid (100 mL) and acetic anhydride (9.8 mL). After stirring at room temperature for 1 h, the reaction was poured into EtOAc and the organic layer was washed with water, saturated $NaHCO_3$, brine, dried ($Na_2SO_4$) and concentrated under vacuum to provide the diacetate, Compound 47 (10.38 g), which was used directly in the next step. $^1$H NMR and LCMS spectra are consistent with structure.

F) Compound 48

N,O-Bis(trimethylsilyl)acetamide (16.4 mL, 66.8 mmol) was added to a suspension of Compound 47 (10.38 g, 15.9 mmol) and uracil (3.6 g, 31.8 mmol) in $CH_3CN$ (100 mL). After heating at 40° C. for 15 minutes to get a clear solution, the reaction was cooled to 0° C. and trimethylsilyl triflate (5.8 mL, 31.8 mmol) was added to the reaction. After heating at 70° C. for 4 hours, the reaction was cooled to room temperature and poured into EtOAc. The organic layer was washed with saturated $NaHCO_3$, brine, dried ($Na_2SO_4$) and concentrated under vacuum to provide crude nucleoside as a monoacetate, which was used without further purification.

The crude nucleoside monoacetate was treated with 7N $NH_3$/MeOH (300 mL) for 12 hours, and then the reaction was concentrated under vacuum. Filtration thru a plug of $SiO_2$ gel and elution with 5% MeOH/EtOAc, provided the nucleoside, Compound 48 (8.46 g, 80% from Compound 47). $^1$H NMR and LCMS spectra are consistent with structure.

G) Compound 49

Compound 48 (7.46 g, 11.3 mmoles) was treated with mercury(II) acetate (7.9 g, 24.8 mmoles) in dichloromethane (125 mL) for 16 hours at room temperature. At that time, saturated NaCl (aq) (30 mL) was added with stirring for 15 minutes. Additional saturated NaCl (aq) was then added and the organic layer was separated, dried ($Na_2SO_4$) and concentrated under vacuum to provide the crude mercurial chloride. The resultant foam was dissolved in toluene (125 mL), and treated with AIBN (100 mg) and tributyltinhydride ($Bu_3SnH$, 7.6 mL, 28.3 mmoles). The reaction proceeded at room temperature for 1 hour and was heated to 50° C. with stirring for an additional 1 hour. Carbon tetrachloride (30 mL) was then added with stirring for 1 hour. Dichloromethane was added, and the organic layer was decanted, washed with water, brine, dried ($Na_2SO_4$) and concentrated under vacuum. Purification by column chromatography ($SiO_2$, eluting with 30% EtOAc/hexanes to 50% EtOAc/hexanes) provided the nucleoside, Compound 49 (5.08 g, 68% from Compound 48). $^1$H NMR and LCMS spectra are consistent with structure.

H) Compound 50

2,3-dichloro-5,6-dicyano-1,4-benzoquinone (DDQ) (2.4 g, 10.6 mmol) was added to a solution of Compound 49 (4.7 g, 7.9 mmol) in dichloromethane (50 mL) and $H_2O$ (3 mL). After stirring for 16 hours, the reaction was concentrated under vacuum and the residue was dissolved in EtOAc. The organic layer was then sequentially washed with water, water:saturated $NaHCO_3$ (1:1), brine, dried ($Na_2SO_4$) and concentrated. Purification by column chromatography ($SiO_2$, using a gradient from 2% to 5% MeOH/$CH_2Cl_2$) provided the nucleoside, Compound 50 (4.1 g, 99%) as a white solid. $^1$H NMR and LCMS spectra are consistent with structure.

I) Compound 51

Triethylamine trihydroflouride (6 mL) was added to a solution of Compound 50 (3.8 g, 7.27 mmol) and triethylamine (2.5 mL) in THF (20 mL) in a polypropylene tube. After stirring at room temperature for 24 hours, the reaction was concentrated under vacuum and water (30 mL) was added with vigourous stirring. The resultant white solid was collected by filtration and dried under vacuum to provide the nucleoside, Compound 51 (1.73 g, 84%) as a white solid. $^1$H NMR and LCMS spectra are consistent with structure.

J) Compound 52

Dimethoxytrityl chloride (2.5 g, 7.4 mmol) was added to a solution of Compound 51 (1.62 g, 5.7 mmoles) in pyridine (30 mL). After stirring at room temperature for 4 hours, the reaction was poured into EtOAc and the organic layer was washed with brine, dried and concentrated. Purification by column chromatography ($SiO_2$, eluting with 30% Acetone/dichloromethane) provided the nucleoside, Compound 52 (3.03 g, 91%) as a solid. $^1$H NMR and LCMS spectra are consistent with structure.

K) Compound 53

2-Cyanoethyl tetraisopropylphorodiamidite (1.1 mL, 3.5 mmol) was added to a solution of Compound 52 (1.35 g, 2.3 mmol), tetrazole (129 mg, 1.8 mmol) and N-methylimidazole (46 μL, 0.58 mmol) in DMF (18 mL). After stirring at room temperature for 6 hours, the reaction was poured into EtOAc and the organic layer was washed with 90% brine, brine, dried ($Na_2SO_4$) and concentrated. Purification by column chromatography ($SiO_2$, eluting with 60% EtOAc/hexanes) provided the phosphoramidite, Compound 53 as a white solid (1.6 g, 94%). $^1$H NMR and LCMS spectra are consistent with structure. $^{31}$P NMR ($CDCl_3$) δ: 150.08, 149.22.

EXAMPLE 7

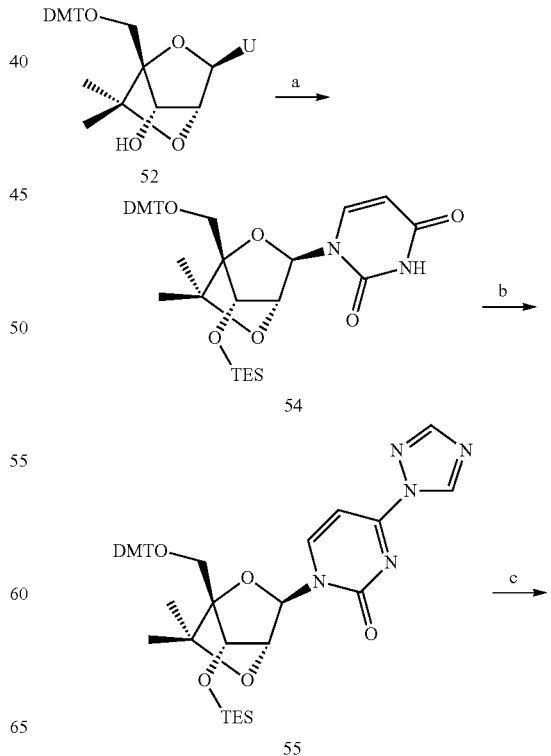

Scheme 7

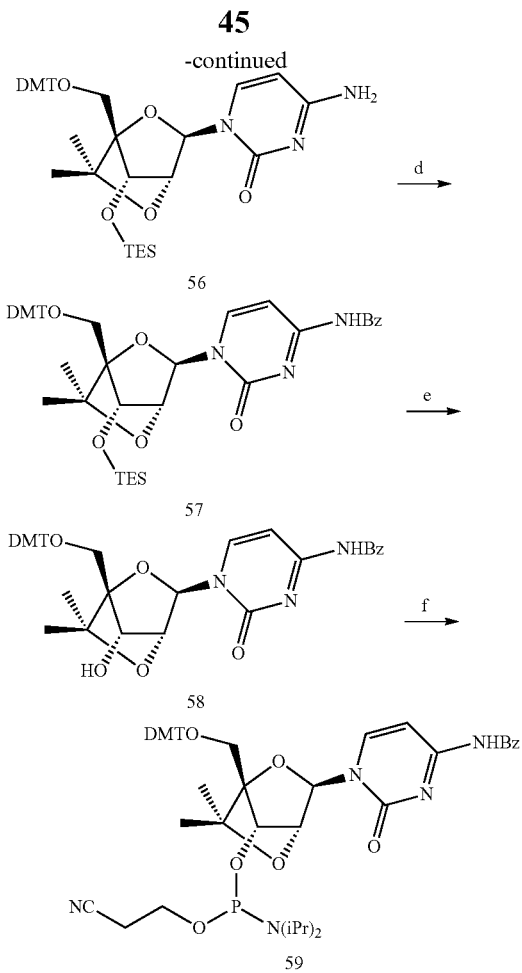

Scheme 6 (a) TESCl, Et₃N, DMAP, CH₂Cl₂, rt; (b) POCl₃, 1,2,4-Triazole, Et₃N, CH₃CN, rt; (c) Aqueous NH₃, 1,4-dioxane, rt; (d) Bz₂O, DMF, rt; (e) Et₃N.3HF, Et₃N, THF, rt; (f) CNCH₂CH₂OP(N-iPr₂)₂, Tetrazole, NMI, DMF.

A) Compound 54

Triethylsilyl chloride (868 uL, 5.17 mmol) was added to a solution of Compound 52 (1.52 g, 2.6 mmol) and imidazole (0.74 g, 10.3 mmol) in DMF (25 mL). After stirring at room temperature for 16 hours, the reaction was poured into EtOAc and the organic phase was sequentially extracted with brine, dried (Na₂SO₄) and concentrated under vacuum. Purification by column chromatography (SiO₂, eluting with 25% to 50% EtOAc/hexanes) provided the nucleoside, Compound 54 (1.7 g, 95%) as a white solid. ¹H NMR and LCMS spectra are consistent with structure.

B) Compound 57

Phosphorus oxychloride (1.8 mL, 19.4 mmol) was added to a cold (0° C.) suspension of 1,2,4-triazole (4 g, 58 mmol) in CH₃CN (25 mL). After stirring for 15 minutes, triethylamine (13.4 mL, 97 mmol) was added to the reaction and the stirring continued for 30 minutes. A solution of Compound 54 (1.7 g, 2.4 mmol) in CH₃CN (20 mL) was added to the reaction at 0° C. After stirring for 10 minutes, the ice bath was removed and the reaction was stirred at room temperature for 4 hours. The solvent was then removed under vacuum and the residue was partitioned between EtOAc and water. The organic layer was then washed with saturated NaHCO₃, brine, dried (Na₂SO₄) and concentrated under vacuum to provide crude Compound 55, which was used without any further purification.

Aqueous ammonia (5 mL) was added to a solution of Compound 55 (from above) in dioxane (20 mL). After stirring at room temperature for 16 hours, the reaction was concentrated under vacuum and dried over high vacuum for 8 hours to provide the nucleoside, Compound 56, which was used without further purification.

Benzoic anhydride (0.814 g, 3.6 mmol) was added to a solution of Compound 56 (from above) in DMF (10 mL). After stirring at room temperature for 16 h, the reaction was poured into EtOAc and the organic layer was extracted with saturated NaHCO₃, brine, dried (Na₂SO₄) and concentrated under vacuum. Purification by column chromatography (SiO₂, eluting with 40% to 60% EtOAc/hexanes) provided the nucleoside, Compound 57 (1.57 g, 81% from Compound 54) as a white solid. ¹H NMR and LCMS spectra are consistent with structure.

C) Compound 58

Triethylamine trihydrofluoride (1.6 mL) was added to a solution of Compound 57 (1.57 g, 1.95 mmol) and triethylamine (0.7 mL) in THF (8 mL) a polypropylene tube. After stirring at room temperature for 16 hours, the reaction was concentrated under vacuum and the residue was dissolved in EtOAc and the organic layer was sequentially washed with water, saturated NaHCO₃, brine, dried (Na₂SO₄) and concentrated under vacuum. Purification by column chromatography (SiO₂, eluting with 10% MeOH/CHCl₃ containing 1% Et₃N) provided the nucleoside, Compound 58 (1.2 g, 89%) as a white solid. ¹H NMR and LCMS spectra are consistent with structure.

D) Compound 59

2-Cyanoethyl tetraisopropylphorodiamidite (0.83 mL, 2.6 mmol) was added to a solution of Compound 58 (1.2 g, 1.7 mmol), tetrazole (91 mg, 1.4 mmol) and N-methylimidazole (34 µL, 0.43 mmol) in DMF (9 mL). After stirring at room temperature for 6 hours, the reaction was poured into EtOAc and the organic layer was washed with 90% brine, brine, dried (Na₂SO₄) and concentrated. Purification by column chromatography (SiO₂, eluting with 60% EtOAc/hexanes) provided the phosphoramidite, Compound 59 as a white solid (0.83 g, 54%). ¹H NMR and LCMS spectra are consistent with structure. ³¹H NMR (CDCl₃) δ: 150.29, 129.51.

EXAMPLE 8

Preparation of Compound 66

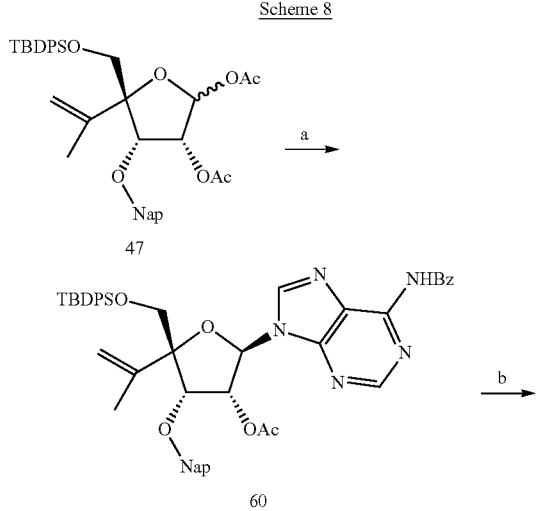

Scheme 8

EXAMPLE 9
Preparation of Compound 73
Scheme 9
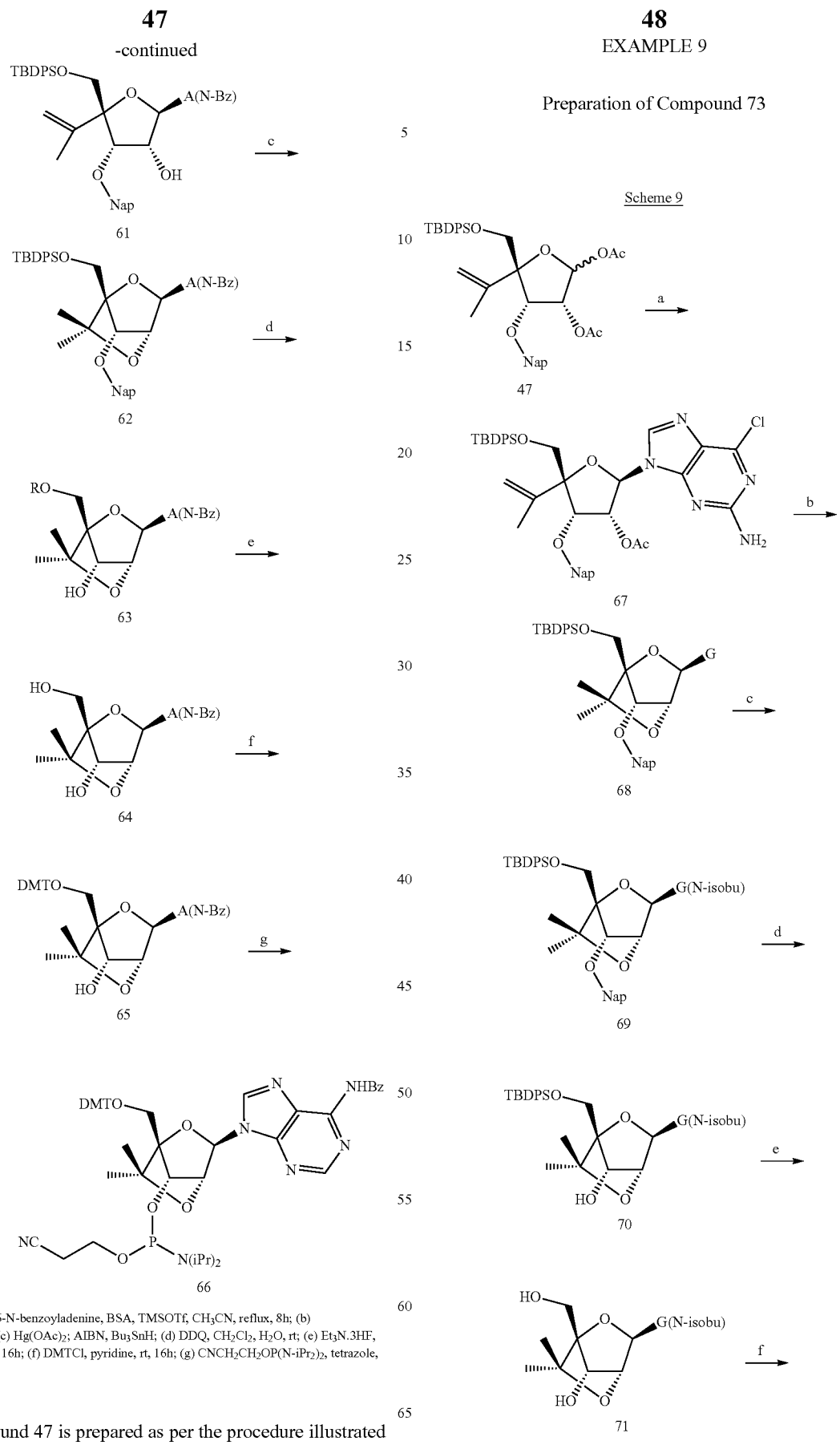
Scheme 8 (a) 6-N-benzoyladenine, BSA, TMSOTf, CH₃CN, reflux, 8h; (b) NH₃/MEOH; (c) Hg(OAc)₂; AIBN, Bu₃SnH; (d) DDQ, CH₂Cl₂, H₂O, rt; (e) Et₃N.3HF, Et₃N, THF, rt, 16h; (f) DMTCl, pyridine, rt, 16h; (g) CNCH₂CH₂OP(N-iPr₂)₂, tetrazole, NMI, DMF.
Compound 47 is prepared as per the procedure illustrated in Example 6.

-continued

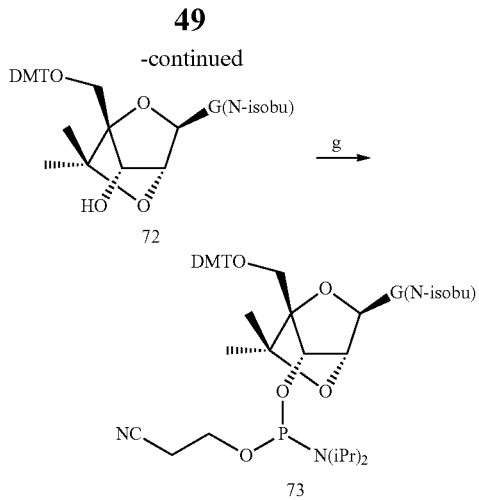

Scheme 9 (a) 2-amino-6-chloropurine, BSA, TMSOTf, CH₃CN, reflux, 2h; (b) 3-hydroxypropionitrile, NaH, THF, 4h; Hg(OAc)₂; AIBN, Bu₃SnH (c) isobutyric anhydride, DMAP, DMF, 60° C., 24h; (d) DDQ, CH₂Cl₂, H₂O, rt, 16h; (e) Et₃N.3HF, Et₃N, THF, rt; (f) DMTCl, pyridine, rt; (g) CNCH₂CH₂OP(N-iPr₂)₂, tetrazole, NMI, DMF.

Compound 47 is prepared as per the procedure illustrated in Example 6.

EXAMPLE 10

Synthesis of Nucleoside Phosphoramidites

The preparation of nucleoside phosphoramidites is performed following procedures that are illustrated herein and in the art such as but not limited to U.S. Pat. No. 6,426,220 and published PCT WO 02/36743.

EXAMPLE 11

Oligonucleotide and Oligonucleoside Synthesis

The oligomeric compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

Oligonucleotides: Unsubstituted and substituted phosphodiester (P=O) oligonucleotides can be synthesized on an automated DNA synthesizer (Applied Biosystems model 394) using standard phosphoramidite chemistry with oxidation by iodine.

Phosphorothioates (P=S) are synthesized similar to phosphodiester oligonucleotides with the following exceptions: thiation is effected by utilizing a 0.2 M solution of phenylacetyl disulfide in 50% 3-picoline in acetonitrile for the oxidation of the phosphite linkages. The thiation reaction step time is increased to 180 sec and preceded by the normal capping step. After cleavage from the CPG column and deblocking in concentrated ammonium hydroxide at 55° C. (12-16 hr), the oligonucleotides are recovered by precipitating with greater than 3 volumes of ethanol from a 1 M NH₄OAc solution. Phosphinate oligonucleotides can be prepared as described in U.S. Pat. No. 5,508,270.

Alkyl phosphonate oligonucleotides can be prepared as described in U.S. Pat. No. 4,469,863.

3'-Deoxy-3'-methylene phosphonate oligonucleotides can be prepared as described in U.S. Pat. No. 5,610,289 or 5,625,050.

Phosphoramidite oligonucleotides can be prepared as described in U.S. Pat. No. 5,256,775 or U.S. Pat. No. 5,366,878.

Alkylphosphonothioate oligonucleotides can be prepared as described in published PCT applications PCT/US94/00902 and PCT/US93/06976 (published as WO 94/17093 and WO 94/02499, respectively).

3'-Deoxy-3'-amino phosphoramidate oligonucleotides can be prepared as described in U.S. Pat. No. 5,476,925.

Phosphotriester oligonucleotides can be prepared as described in U.S. Pat. No. 5,023,243.

Borano phosphate oligonucleotides can be prepared as described in U.S. Pat. Nos. 5,130,302 and 5,177,198.

Oligonucleosides: Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone oligomeric compounds having, for instance, alternating MMI and P=O or P=S linkages can be prepared as described in U.S. Pat. Nos. 5,378,825; 5,386,023; 5,489,677; 5,602,240 and 5,610,289.

Formacetal and thioformacetal linked oligonucleosides can be prepared as described in U.S. Pat. Nos. 5,264,562 and 5,264,564.

Ethylene oxide linked oligonucleosides can be prepared as described in U.S. Pat. No. 5,223,618.

EXAMPLE 12

Oligonucleotide Isolation

After cleavage from the controlled pore glass solid support and deblocking in concentrated ammonium hydroxide at 55° C. for 12-16 hours, the oligonucleotides or oligonucleosides are recovered by precipitation out of 1 M NH₄OAc with >3 volumes of ethanol. Synthesized oligonucleotides are analyzed by electrospray mass spectroscopy (molecular weight determination) and by capillary gel electrophoresis. The relative amounts of phosphorothioate and phosphodiester linkages obtained in the synthesis is determined by the ratio of correct molecular weight relative to the −16 amu product (+/−32+/−48). For some studies oligonucleotides are purified by HPLC, as described by Chiang et al., J. Biol. Chem. 1991, 266, 18162-18171. Results obtained with HPLC-purified material are generally similar to those obtained with non-HPLC purified material.

EXAMPLE 13

Oligonucleotide Synthesis

96 Well Plate Format

Oligonucleotides can be synthesized via solid phase P(III) phosphoramidite chemistry on an automated synthesizer capable of assembling 96 sequences simultaneously in a 96-well format. Phosphodiester internucleotide linkages are afforded by oxidation with aqueous iodine. Phosphorothioate internucleotide linkages are generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites are purchased from commercial vendors (e.g. PE-Applied Biosystems, Foster City, Calif., or Pharmacia, Piscataway, N.J.). Non-standard nucleosides are synthesized as per standard or patented methods. They are utilized as base protected beta-cyanoethyldiisopropyl phosphoramidites.

Oligonucleotides are cleaved from support and deprotected with concentrated $NH_4OH$ at elevated temperature (55-60° C.) for 12-16 hours and the released product then dried in vacuo. The dried product is then re-suspended in sterile water to afford a master plate from which all analytical and test plate samples are then diluted utilizing robotic pipettors.

EXAMPLE 14

Oligonucleotide Analysis Using 96-Well Plate Format

The concentration of oligonucleotide in each well is assessed by dilution of samples and UV absorption spectroscopy. The full-length integrity of the individual products is evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition is confirmed by mass analysis of the oligomeric compounds utilizing electrospray-mass spectroscopy. All assay test plates are diluted from the master plate using single and multi-channel robotic pipettors. Plates are judged to be acceptable if at least 85% of the oligomeric compounds on the plate are at least 85% full length.

EXAMPLE 15

Cell Culture and Oligonucleotide Treatment

The effect of oligomeric compounds on target nucleic acid expression can be tested in any of a variety of cell types provided that the target nucleic acid is present at measurable levels. This can be routinely determined using, for example, PCR or Northern blot analysis. Cell lines derived from multiple tissues and species can be obtained from American Type Culture Collection (ATCC, Manassas, Va.).

The following cell type is provided for illustrative purposes, but other cell types can be routinely used, provided that the target is expressed in the cell type chosen. This can be readily determined by methods routine in the art, for example Northern blot analysis, ribonuclease protection assays or RT-PCR.

B.END cells: The mouse brain endothelial cell line b.END was obtained from Dr. Werner Risau at the Max Plank Institute (Bad Nauheim, Germany). b.END cells were routinely cultured in DMEM, high glucose (Invitrogen Life Technologies, Carlsbad, Calif.) supplemented with 10% fetal bovine serum (Invitrogen Life Technologies, Carlsbad, Calif.). Cells were routinely passaged by trypsinization and dilution when they reached approximately 90% confluence. Cells were seeded into 96-well plates (Falcon-Primaria #353872, BD Biosciences, Bedford, Mass.) at a density of approximately 3000 cells/well for uses including but not limited to oligomeric compound transfection experiments.

Experiments involving treatment of cells with oligomeric compounds:

When cells reach appropriate confluency, they are treated with oligomeric compounds using a transfection method as described.

LIPOFECTIN™

When cells reached 65-75% confluency, they are treated with oligonucleotide. Oligonucleotide is mixed with LIPOFECTIN™ Invitrogen Life Technologies, Carlsbad, Calif.) in Opti-MEM™-1 reduced serum medium (Invitrogen Life Technologies, Carlsbad, Calif.) to achieve the desired concentration of oligonucleotide and a LIPOFECTIN™ concentration of 2.5 or 3 µg/mL per 100 nM oligonucleotide. This transfection mixture is incubated at room temperature for approximately 0.5 hours. For cells grown in 96-well plates, wells are washed once with 100 µL OPTI-MEM™-1 and then treated with 130 µL of the transfection mixture. Cells grown in 24-well plates or other standard tissue culture plates are treated similarly, using appropriate volumes of medium and oligonucleotide. Cells are treated and data are obtained in duplicate or triplicate. After approximately 4-7 hours of treatment at 37° C., the medium containing the transfection mixture is replaced with fresh culture medium. Cells are harvested 16-24 hours after oligonucleotide treatment.

Other suitable transfection reagents known in the art include, but are not limited to, CYTOFECTIN™, LIPOFECTAMINE™, OLIGOFECTAMINE™, and FUGENE™. Other suitable transfection methods known in the art include, but are not limited to, electroporation.

EXAMPLE 16

Analysis of Oligonucleotide Inhibition of a Target Expression

Antisense modulation of a target expression can be assayed in a variety of ways known in the art. For example, a target mRNA levels can be quantitated by, e.g., Northern blot analysis, competitive polymerase chain reaction (PCR), or real-time PCR. Real-time quantitative PCR is presently desired. RNA analysis can be performed on total cellular RNA or poly(A)+ mRNA. One method of RNA analysis is the use of total cellular RNA as described in other examples herein. Methods of RNA isolation are well known in the art. Northern blot analysis is also routine in the art. Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of a target can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Methods for preparation of polyclonal antisera are taught in, for example, Ausubel, F. M. et al., *Current Protocols in Molecular Biology*, Volume 2, pp. 11.12.1-11.12.9, John Wiley & Sons, Inc., 1997. Preparation of Monoclonal Antibodies is Taught in, for Example, Ausubel, F. M. et al., *Current Protocols in Molecular Biology*, Volume 2, pp. 11.4.1-11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1-10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1-10.8.21, John Wiley & Sons, Inc., 1997. Enzyme-linked immunosorbent assays (ELISA) are standard in the art and can be found at, for example, Ausubel, F. M. et al., *Current Protocols in Molecular Biology*, Volume 2, pp. 11.2.1-11.2.22, John Wiley & Sons, Inc., 1991.

EXAMPLE 17

Design of Phenotypic Assays and In Vivo Studies for the Use of Target Inhibitors Phenotypic Assays Once target inhibitors have been identified by the methods disclosed herein, the oligomeric compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of a target in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with a target inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Measurement of the expression of one or more of the genes of the cell after treatment is also used as an indicator of the efficacy or potency of the a target inhibitors. Hallmark genes, or those genes suspected to be associated with a specific disease state, condition, or phenotype, are measured in both treated and untreated cells.

In Vivo Studies

The individual subjects of the in vivo studies described herein are warm-blooded vertebrate animals, which includes humans.

EXAMPLE 18

RNA Isolation

Poly(A)+ mRNA Isolation

In certain embodiments, poly(A)+ mRNA is isolated according to Miura et al., (Clin. Chem., 1996, 42, 1758-1764). Other methods for poly(A)+ mRNA isolation are routine in the art. Briefly, for cells grown on 96-well plates, growth medium is removed from the cells and each well is washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) is added to each well, the plate is gently agitated and then incubated at room temperature for five minutes. 55 of lysate is transferred to Oligo d(T) coated 96-well plates (AGCT Inc., Irvine Calif.). Plates are incubated at room temperature for 60 minutes and washed 3 times with 200 µL of wash buffer (10 mM Tris-HCl pH 7.6, 1 mM EDTA, 0.3 M NaCl). After the final wash, the plate is blotted on paper towels to remove excess wash buffer and then air-dried for 5 minutes. 60 µL of elution buffer (5 mM Tris-HCl pH 7.6), preheated to 70° C., is added to each well, the plate is incubated on a 90° C. hot plate for 5 minutes, and the eluate is then transferred to a fresh 96-well plate.

Cells grown on 100 mm or other standard plates may be treated similarly, using appropriate volumes of all solutions.

Total RNA Isolation

Total RNA is isolated using an RNEASY 96™ kit and buffers purchased from Qiagen Inc. (Valencia, Calif.) following the manufacturer's recommended procedures. Briefly, for cells grown on 96-well plates, growth medium is removed from the cells and each well is washed with 200 µL cold PBS. 150 µL Buffer RLT is added to each well and the plate vigorously agitated for 20 seconds. 150 µL of 70% ethanol is then added to each well and the contents mixed by pipetting three times up and down. The samples are then transferred to the RNEASY 96™ well plate attached to a QIAVAC™ manifold fitted with a waste collection tray and attached to a vacuum source. Vacuum is applied for 1 minute. 5004 of Buffer RW1 is added to each well of the RNEASY 96™ plate and incubated for 15 minutes and the vacuum is again applied for 1 minute. An additional 500 µL of Buffer RW1 is added to each well of the RNEASY 96™ plate and the vacuum is applied for 2 minutes. 1 mL of Buffer RPE is then added to each well of the RNEASY 96™ plate and the vacuum applied for a period of 90 seconds. The Buffer RPE wash is then repeated and the vacuum is applied for an additional 3 minutes. The plate is then removed from the QIAVAC™ manifold and blotted dry on paper towels. The plate is then re-attached to the QIAVAC™ manifold fitted with a collection tube rack containing 1.2 mL collection tubes. RNA is then eluted by pipetting 140 µL of RNAse free water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

EXAMPLE 19

Real-time Quantitative PCR Analysis of Target mRNA Levels

In certain embodiments, quantitation of a target mRNA levels is accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

RT and PCR reagents are obtained from Invitrogen Life Technologies (Carlsbad, Calif.). RT, real-time PCR is carried out by adding 20 µL PCR cocktail (2.5×PCR buffer minus $MgCl_2$, 6.6 mM $MgCl_2$, 375 µM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5× ROX dye) to 96-well plates containing 30 µL total RNA solution (20-200 ng). The room temperature reaction is carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

In certain embodiments, gene target quantities obtained by RT, real-time PCR are normalized using either the expression level of GAPDH, a gene whose expression is constant, or by quantifying total RNA using RIBOGREEN™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent (Molecular Probes, Inc. Eugene, Oreg.). Methods of RNA quantification by RIBOGREEN™ are taught in Jones, L. J., et al, (Analytical Biochemistry, 1998, 265, 368-374).

In this assay, 170 µL of RIBOGREEN™ working reagent (RIBOGREEN™ reagent diluted 1:350 in 10 mM Tris-HCl, 1 mM EDTA, pH 7.5) is pipetted into a 96-well plate containing 30 µL purified, cellular RNA. The plate is read in a CytoFluor 4000 (PE Applied Biosystems) with excitation at 485 nm and emission at 530 nm.

EXAMPLE 20

Target-Specific Primers and Probes

Probes and primers may be designed to hybridize to a target sequence, using published sequence information.

For example, for human PTEN, the following primer-probe set was designed using published sequence information (GENBANK™ accession number U92436.1, SEQ ID NO: 01).

```
                                       (SEQ ID NO: 02)
    Forward primer:    AATGGCTAAGTGAAGATGACAATCAT (SEQ ID NO: 03)
    Reverse primer:    TGCACATATCATTACACCAGTTCGT
```

And the PCR probe:
FAM-TTGCAGCAATTCACTGTAAAGCTG-GAAAGG-TAMRA (SEQ ID NO: 04), where FAM is the fluorescent dye and TAMRA is the quencher dye.

EXAMPLE 21

Western Blot Analysis of Target Protein Levels

Western blot analysis (immunoblot analysis) is routinely carried out using standard methods. Cells are harvested 16-20 h after oligonucleotide treatment, washed once with PBS, suspended in Laemmli buffer (100 µl/well), boiled for 5 minutes and loaded on a 16% SDS-PAGE gel. Gels are run for 1.5 hours at 150 V, and transferred to membrane for western blotting. Appropriate primary antibody directed to a target is used, with a radiolabeled or fluorescently labeled secondary antibody directed against the primary antibody species. Bands are visualized using a PHOSPHORIMAGER™ (Molecular Dynamics, Sunnyvale Calif.).

EXAMPLE 22

Effects of Antisense Compounds Targeting PTEN In Vivo Study

Six week old male Balb/c mice (Jackson Laboratory, Bar Harbor, Me.) were injected once with modified oligomers targeted to PTEN at doses of 3.2, 10, 32 and 100 mg/kg. The mice were sacrificed 64 hours following the final administration. Liver tissues were homogenized and PTEN mRNA levels were quantitated using real-time PCR and RIBOGREEN® RNA quantification reagent (Molecular Probes, Inc. Eugene, Oreg.) according to standard protocols. PTEN mRNA levels were determined relative to total RNA (using Ribogreen), prior to normalization to saline-treated control. The relative activities of the antisense compounds are shown below with the results presented as the average % inhibition of mRNA expression for each antisense compound, normalized to saline-injected control.

| SEQ ID NO/ | | PTEN % Inhibition (mg/kg dose) | | | |
|---|---|---|---|---|---|
| ISIS NO | Sequence | 3.2 | 10 | 32 | 100 |
| 05/425453 | C$_l$U$_l$TAGCACTGGCC$_l$U$_l$ | 7 | 20 | 64 | 93 |
| 06/392063 | $^{Me}$C$_1$T$_1$TAGCACTGG C$^{Me}$C$_1$T$_1$ | 8 | 71 | 93 | 93 |

Each internucleoside linking group is a phosphorothioate, each nucleoside not otherwise annotated is a 2'-deoxyribonucleoside, each $^{Me}$C is a 5-CH$_3$C, and nucleosides followed by a subscript i or l are defined as shown below:

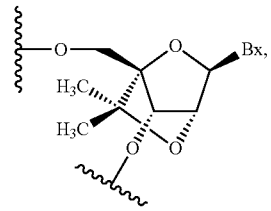

subscript i

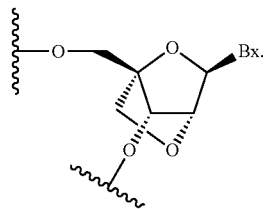

subscript l

ALT and AST levels were measured in mice treated with the antisense oligomers 394425, 411001 and 425-453. Serum was analyzed by LabCorp Testing Facility (San Diego, Calif.) and ALT and AST levels in serum were measured relative to saline injected mice. The approximate ALT and AST levels are listed in the table below.

| SEQ ID NO/ ISIS NO | Dose (mg/kg) | ALT (IU/L) | AST (IU/L) | ED$_{50}$ | Tm ° C. |
|---|---|---|---|---|---|
| 05/425453 | na | | | 20.8 | 56.3 |
| | 3.2 | 26 | 49 | | |
| | 10 | 28 | 52 | | |
| | 32 | 23 | 51 | | |
| | 100 | 22.5 | 55.5. | | |
| 06/392063 | na | | | 7.0 | 60.5 |
| | 3.2 | 9.5 | 56.75 | | |
| | 10 | 12.5 | 86.25 | | |
| | 32 | 9.75 | 81 | | |
| | 100 | 18670.8 | 27398.5 | | |
| Saline | | 14 | 60.5. | | |

All publications, patents, and patent applications referenced herein are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A bicyclic nucleoside having Formula I:

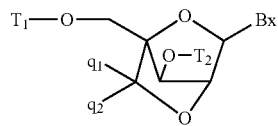

wherein:
Bx is a heterocyclic base moiety;
one of $T_1$ and $T_2$ is H or a hydroxyl protecting group and the other of $T_1$ and $T_2$ is H, a hydroxyl protecting group or a reactive phosphorus group;
$q_1$ and $q_2$ are each, independently, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_1$, $SJ_1$, $SOJ_1$, $SO_2J_1$, $NJ_1J_2$, $N_3$, CN, C(=O)$OJ_1$, C(=O)$NJ_1J_2$, C(=O)$J_1$, O—C(=O)$NJ_1J_2$, N(H)C(=NH)$NJ_1J_2$, N(H)C(=O)$NJ_1J_2$ or N(H)C(=S)$NJ_1J_2$;
or $q_1$ and $q_2$ together are =C($q_3$)($q_4$);
$q_3$ and $q_4$ are each, independently, H, halogen, $C_1$-$C_{12}$ alkyl or substituted $C_1$-$C_{12}$ alkyl;
each substituted group is, independently, mono or poly substituted with substituent groups independently selected from halogen, $C_1$-$C_6$ alkyl, $C_2$-$C_6$ alkenyl, $C_2$-$C_6$ alkynyl, $OJ_1$, $SJ_1$, $NJ_1J_2$, $N_3$, CN, C(=O)$OJ_1$, C(=O)$NJ_1J_2$, C(=O)$J_1$, O—C(=O)$NJ_1J_2$, N(H)C(=O)$NJ_1J_2$ or N(H)C(=S)$NJ_1J_2$; and
each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group.

2. The bicyclic nucleoside of claim 1 wherein $q_1$ and $q_2$ are each, independently, $C_1$-$C_6$ alkyl or substituted $C_1$-$C_6$ alkyl.

3. The bicyclic nucleoside of claim 1 wherein $q_1$ and $q_2$ are each, independently, methyl, ethyl or propyl.

4. The bicyclic nucleoside of claim 1 wherein $q_1$ and $q_2$ are each methyl.

5. The bicyclic nucleoside of claim 1 wherein at least one of $q_1$ and $q_2$ is substituted $C_1$-$C_6$ alkyl.

6. The bicyclic nucleoside of claim 5 wherein said substituted $C_1$-$C_6$ alkyl comprises at least one substituent group selected from $OJ_1$, $NJ_1J_2$ or CN wherein each $J_1$ and $J_2$ is, independently, H, $C_1$-$C_6$ alkyl or a protecting group.

7. The bicyclic nucleoside of claim 1 wherein $q_1$ and $q_2$ together, are =C($q_3$)($q_4$).

8. The bicyclic nucleoside of claim 7 wherein $q_3$ and $q_4$ are each H.

9. The bicyclic nucleoside of claim 1 wherein each of $T_1$ and $T_2$ is a hydroxyl protecting group.

10. The bicyclic nucleoside of claim 1 wherein $T_1$ is 4,4'-dimethoxytrityl and $T_2$ is diisopropylcyanoethoxy phosphoramidite.

11. The bicyclic nucleoside of claim 10 wherein $q_1$ and $q_2$ are each methyl.

12. The bicyclic nucleoside of claim 10 wherein $q_1$ and $q_2$ together, are =C($q_3$)($q_4$) and $q_3$ and $q_4$ are each H.

13. The bicyclic nucleoside of claim 1 wherein Bx is a pyrimidine, substituted pyrimidine, purine or substituted purine.

14. The bicyclic nucleoside of claim 1 wherein Bx is uracil, 5-propynyl-uracil, 5-thiazolo-uracil, thymine, cytosine, 5-methylcytosine, 5-propynyl-cytosine, 5-thiazolo-cytosine, adenine, guanine or 2,6-diaminopurine.

15. The bicyclic nucleoside of claim 1 having Formula II:

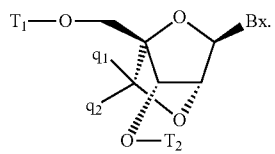

16. An oligomeric compound comprising at least one bicyclic nucleoside having Formula III:

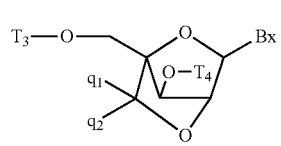

wherein independently for each bicyclic nucleoside having Formula III:
Bx is a heterocyclic base moiety;
one of $T_3$ and $T_4$ is an internucleoside linking group linking the bicyclic nucleoside to the oligomeric compound and the other of $T_3$ and $T_4$ is H, a hydroxyl protecting group, a linked conjugate group, a 5' or 3'-terminal group or an internucleoside linking group linking the bicyclic nucleoside to the oligomeric compound;
$q_1$ and $q_2$ are each, independently, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_1$, $SJ_1$, $SOJ_1$, $SO_2J_1$, $NJ_1J_2$, $N_3$, CN, C(=O)$OJ_1$, C(=O)$NJ_1J_2$, C(=O)$J_1$, O—C(=O)$NJ_1J_2$, N(H)C(=NH)$NJ_1J_2$, N(H)C(=O)$NJ_1J_2$ or N(H)C(=S)$NJ_1J_2$;
or $q_1$ and $q_2$ together are =C($q_3$)($q_4$);
$q_3$ and $q_4$ are each, independently, H, halogen, $C_1$-$C_{12}$ alkyl or substituted $C_1$-$C_{12}$ alkyl;
each substituted group is, independently, mono or poly substituted with substituent groups independently selected from halogen, $C_1$-$C_6$ alkyl, $C_2$-$C_6$ alkenyl, $C_2$-$C_6$ alkynyl, $OJ_1$, $SJ_1$, $NJ_1J_2$, $N_3$, CN, C(=O)$OJ_1$, C(=O)$NJ_1J_2$, C(=O)$J_1$, O—C(=O)$NJ_1J_2$, N(H)C(=O)$NJ_1J_2$ or N(H)C(=S)$NJ_1J_2$;
each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group; and
wherein said oligomeric compound comprises from 8 to about 40 linked nucleosides.

17. The oligomeric compound of claim 16 wherein $q_1$ and $q_2$ are each, independently, $C_1$-$C_6$ alkyl or substituted $C_1$-$C_6$ alkyl for each bicyclic nucleoside having Formula III.

18. The oligomeric compound of claim 16 wherein $q_1$ and $q_2$ are each, independently, methyl, ethyl or propyl for each bicyclic nucleoside having Formula III.

19. The oligomeric compound of claim 16 wherein $q_1$ and $q_2$ are each methyl for each bicyclic nucleoside having Formula III.

20. The oligomeric compound of claim 16 wherein at least one of $q_1$ and $q_2$ is substituted $C_1$-$C_6$ alkyl for each bicyclic nucleoside having Formula III.

21. The oligomeric compound of claim 16 wherein at least one of $q_1$ and $q_2$ is substituted $C_1$-$C_6$ alkyl for each bicyclic nucleoside having Formula III wherein the substituent group is selected from $OJ_1$, $NJ_1J_2$ or CN wherein each $T_1$ and $J_2$ is, independently, H, $C_1$-$C_6$ alkyl or a protecting group.

22. The oligomeric compound of claim 16 wherein $q_1$ and $q_2$ together are =C($q_3$)($q_4$) for each bicyclic nucleoside having Formula III.

23. The oligomeric compound of claim 22 wherein $q_3$ and $q_4$ are each H for each bicyclic nucleoside having Formula III.

24. The oligomeric compound of claim 22 wherein at least one of $q_3$ and $q_4$ is halogen, $C_1$-$C_6$ alkyl or substituted $C_1$-$C_6$ alkyl for each bicyclic nucleoside having Formula III.

25. The oligomeric compound of claim 16 comprising at least one 3' or 5'-terminal group.

26. The oligomeric compound of claim 16 wherein each internucleoside linking group is, independently, phosphodiester or phosphorothioate.

27. The oligomeric compound of claim 16 wherein each internucleoside linking group is a phosphorothioate.

28. The oligomeric compound of claim 16 wherein each bicyclic nucleoside has Formula IV:

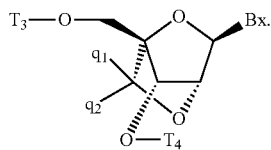

IV

29. The oligomeric compound of claim 16 comprising at least one region of at least two contiguous bicyclic nucleosides having Formula III located at either the 3' or the 5'-end of the oligomeric compound.

30. The oligomeric compound of claim 16 comprising two external regions, each independently comprising from 1 to about 5 contiguous bicyclic nucleosides having Formula III, wherein one of the external regions is located at the 5'-end and the other external region is located at the 3'-end and wherein the two external regions are separated by an internal region comprising from about 6 to about 14 monomeric subunits.

31. The oligomeric compound of claim 30 wherein essentially each monomeric subunit in the internal region is a β-D-2'-deoxyribonucleoside.

32. The oligomeric compound of claim 30 wherein the internal region comprises from about 8 to about 14 β-D-2'-deoxyribonucleosides.

33. The oligomeric compound of claim 30 wherein each external region independently comprises from 2 to about 3 bicyclic nucleosides having Formula III.

34. The oligomeric compound of claim 16 comprising from about 8 to about 20 monomer subunits in length.

35. The oligomeric compound of claim 16 comprising from about 10 to about 16 monomer subunits in length.

36. The oligomeric compound of claim 16 comprising from about 10 to about 14 monomer subunits in length.

37. A method of inhibiting gene expression comprising contacting one or more cells, a tissue or an animal with an oligomeric compound of claim 16 wherein said oligomeric compound is complementary to a target RNA.

38. The method of claim 37 wherein said cells are in an animal.

39. The method of claim 37 wherein said cells are in a human.

40. The method of claim 37 wherein said target RNA is mRNA, pre-mRNA or micro RNA.

41. The method of claim 37 wherein said target RNA is mRNA.

42. The method of claim 37 wherein said target RNA is human mRNA.

43. The method of claim 37 wherein said target RNA is cleaved thereby inhibiting its function.

44. The method of claim 37 further comprising detecting the levels of target RNA.

* * * * *

SEQUENCE LISTING

<160> NUMBER OF SEQ ID NOS: 6

<210> SEQ ID NO 1
<211> LENGTH: 3160
<212> TYPE: DNA
<213> ORGANISM: H. Sapiens

<400> SEQUENCE: 1

```
cctccctcg cccggcgcgg tcccgtccgc ctctcgctcg cctcccgcct ccccctcggtc     60 ttccgaggcg cccgggctcc cggcgcggcg gcggaggggg cgggcaggcc ggcgggcggt    120
gatgtggcag gactctttat gcgctgcggc aggatacgcg ctcggcgctg ggacgcgact    180
gcgctcagtt ctctcctctc ggaagctgca gccatgatgg aagtttgaga gttgagccgc    240
tgtgaggcga ggccgggctc aggcgaggga gatgagagac ggcggcggcc gcggcccgga    300 gccctctca gcgcctgtga gcagccgcgg gggcagcgcc ctcggggagc cggccggcct    360
gcggcggcgg cagcggcggc gtttctgcc tcctcttcgt cttttctaac cgtgcagcct    420
cttcctcggc ttctcctgaa agggaaggtg gaagccgtgg gctcgggcgg gagccggctg    480
```

| | |
|---|---|
| aggcgcggcg gcggcggcgg cggcacctcc cgctcctgga gcggggggga gaagcggcgg | 540 |
| cggcggcggc cgcggcggct gcagctccag ggaggggggtc tgagtcgcct gtcaccattt | 600 |
| ccagggctgg gaacgccgga gagttggtct ctcccctctct actgcctcca acacggcggc | 660 |
| ggcggcggc gcacatccag ggacccgggc cggttttaaa cctcccgtcc gccgccgccg | 720 |
| cacccccgt ggcccgggct ccggaggccg ccggcggagg cagccgttcg gaggattatt | 780 |
| cgtcttctcc ccattccgct gccgccgctg ccaggcctct ggctgctgag gagaagcagg | 840 |
| cccagtcgct gcaaccatcc agcagccgcc gcagcagcca ttacccggct gcggtccaga | 900 |
| gccaagcggc ggcagagcga ggggcatcag ctaccgccaa gtccagagcc atttccatcc | 960 |
| tgcagaagaa gccccgccac cagcagcttc tgccatctct ctcctccttt tcttcagcc | 1020 |
| acaggctccc agacatgaca gccatcatca aagagatcgt tagcagaaac aaaaggagat | 1080 |
| atcaagagga tggattcgac ttagacttga cctatattta tccaaacatt attgctatgg | 1140 |
| gatttcctgc agaaagactt gaaggcgtat acaggaacaa tattgatgat gtagtaaggt | 1200 |
| ttttggattc aaagcataaa aaccattaca agatatacaa tctttgtgct gaaagacatt | 1260 |
| atgacaccgc caaatttaat tgcagagttg cacaatatcc ttttgaagac cataacccac | 1320 |
| cacagctaga acttatcaaa cccttttgtg aagatcttga ccaatggcta agtgaagatg | 1380 |
| acaatcatgt tgcagcaatt cactgtaaag ctggaaaggg acgaactggt gtaatgatat | 1440 |
| gtgcatattt attacatcgg ggcaaatttt taaaggcaca agaggcccta gatttctatg | 1500 |
| gggaagtaag gaccagagac aaaaagggag taactattcc cagtcagagg cgctatgtgt | 1560 |
| attattatag ctacctgtta aagaatcatc tggattatag accagtggca ctgttgtttc | 1620 |
| acaagatgat gtttgaaact attccaatgt tcagtggcgg aacttgcaat cctcagtttg | 1680 |
| tggtctgcca gctaaaggtg aagatatatt cctccaattc aggacccaca cgacgggaag | 1740 |
| acaagttcat gtactttgag ttccctcagc cgttacctgt gtgtggtgat atcaaagtag | 1800 |
| agttcttcca caaacagaac aagatgctaa aaaaggacaa aatgtttcac ttttgggtaa | 1860 |
| atacattctt cataccagga ccagaggaaa cctcagaaaa agtagaaaat ggaagtctat | 1920 |
| gtgatcaaga aatcgatagc atttgcagta tagagcgtgc agataatgac aaggaatatc | 1980 |
| tagtacttac tttaacaaaa aatgatcttg acaaagcaaa taaagacaaa gccaaccgat | 2040 |
| acttttctcc aaattttaag gtgaagctgt acttcacaaa aacagtagag gagccgtcaa | 2100 |
| atccagaggc tagcagttca acttctgtaa caccagatgt tagtgacaat gaacctgatc | 2160 |
| attatagata ttctgacacc actgactctg atccagagaa tgaaccttt gatgaagatc | 2220 |
| agcatacaca aattacaaaa gtctgaattt tttttatca agagggataa acaccatga | 2280 |
| aaataaactt gaataaactg aaaatggacc ttttttttt taatgcaat aggacattgt | 2340 |
| gtcagattac cagttatagg aacaattctc ttttcctgac caatcttgtt ttaccctata | 2400 |
| catccacagg gttttgacac ttgttgtcca gttgaaaaaa ggttgtgtag ctgtgtcatg | 2460 |
| tatataccct tttgtgtcaa aaggacattt aaaattcaat taggattaat aaagatggca | 2520 |
| ctttcccgtt ttattccagt tttataaaaa gtggagacag actgatgtgt atacgtagga | 2580 |
| atttttcct tttgtgttct gtcaccaact gaagtggcta aagagctttg tgatatactg | 2640 |
| gttcacatcc tacccctttg cacttgtggc aacagataag tttgcagttg gctaagagag | 2700 |
| gtttccgaaa ggttttgcta ccattctaat gcatgtattc gggttagggc aatggagggg | 2760 |
| aatgctcaga aaggaaataa ttttatgctg gactctggac catataccat ctccagctat | 2820 |
| ttacacacac ctttctttag catgctacag ttattaatct ggacattcga ggaattggcc | 2880 |

```
                                         -continued
gctgtcactg cttgttgttt gcgcattttt ttttaaagca tattggtgct agaaaaggca    2940
gctaaaggaa gtgaatctgt attggggtac aggaatgaac cttctgcaac atcttaagat    3000
ccacaaatga agggatataa aaataatgtc ataggtaaga acacagcaa caatgactta     3060 accatataaa tgtggaggct atcaacaaag aatgggcttg aaacattata aaaattgaca    3120
atgatttatt aaatatgttt tctcaattgt aaaaaaaaa                           3160

<210> SEQ ID NO 2
<211> LENGTH: 26
<212> TYPE: DNA
<213> ORGANISM: Artificial Sequence
<220> FEATURE:
<223> OTHER INFORMATION: Primer

<400> SEQUENCE: 2
aatggctaag tgaagatgac aatcat                                         26

<210> SEQ ID NO 3
<211> LENGTH: 25
<212> TYPE: DNA
<213> ORGANISM: Artificial Sequence
<220> FEATURE:
<223> OTHER INFORMATION: Primer

<400> SEQUENCE: 3
tgcacatatc attacaccag ttcgt                                          25

<210> SEQ ID NO 4
<211> LENGTH: 30
<212> TYPE: DNA
<213> ORGANISM: Artificial Sequence
<220> FEATURE:
<223> OTHER INFORMATION: Probe

<400> SEQUENCE: 4
ttgcagcaat tcactgtaaa gctggaaagg                                     30

<210> SEQ ID NO 5
<211> LENGTH: 14
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)...(12)
<223> OTHER INFORMATION: Bases at these positions are RNA

<400> SEQUENCE: 5
cutagcactg gccu                                                      14

<210> SEQ ID NO 6
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 6
cttagcactg gcct                                                      14
```